(12) United States Patent
Lamb et al.

(10) Patent No.: US 12,300,393 B2
(45) Date of Patent: *May 13, 2025

(54) DEVICE AND METHODS FOR MACHINE LEARNING-DRIVEN DIAGNOSTIC TESTING

(71) Applicant: GE Precision Healthcare LLC, Wauwatosa, WI (US)

(72) Inventors: David Lamb, Cary, IL (US); Bryan Cobb, Cape Elizabeth, ME (US); Paul Mullen, Waukesha, WI (US)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 340 days.

This patent is subject to a terminal disclaimer.

(21) Appl. No.: 17/804,781

(22) Filed: May 31, 2022

(65) Prior Publication Data
US 2022/0293285 A1 Sep. 15, 2022

Related U.S. Application Data

(60) Division of application No. 16/198,709, filed on Nov. 21, 2018, now Pat. No. 11,373,761, which is a (Continued)

(51) Int. Cl.
*G16H 80/00* (2018.01)
*G06N 7/01* (2023.01)
(Continued)

(52) U.S. Cl.
CPC ............. *G16H 80/00* (2018.01); *G06N 7/01* (2023.01); *G16H 10/40* (2018.01); *G16H 50/30* (2018.01)

(58) Field of Classification Search
None
See application file for complete search history.

(56) References Cited

U.S. PATENT DOCUMENTS

2004/0172294 A1 9/2004 Dahlin et al.
2005/0075543 A1 4/2005 Calabrese
(Continued)

FOREIGN PATENT DOCUMENTS

WO 2019246581 A1 12/2019

OTHER PUBLICATIONS

"SMS Marketing: iOS Previews and Google Analytics Tracking," Listrak Website, Available Online at https://www.istrak.com/blog/sms-marketing-ios-previews-and-google-analytics-tracking, Dec. 14, 2017, 6 pages.

*Primary Examiner* — Devin C Hein
(74) *Attorney, Agent, or Firm* — McCoy Russell LLP

(57) ABSTRACT

Various devices and methods are provided for machine learning-driven medical diagnostic testing. In one example, a method includes generating a patient-specific collaboration channel comprising a patient-specific dashboard and a communication thread between a care provider team monitoring a patient and a virtual healthcare assistant, storing, at the channel, text- and/or rich media-based messages on the communication thread between one or more care providers of the care provider team and the virtual healthcare assistant, at least a portion of the messages on the communication thread including patient-specific medical data, and responsive to a prompt, outputting at least a portion of the communication thread that includes the patient-specific medical data to a display device.

15 Claims, 13 Drawing Sheets

Related U.S. Application Data continuation-in-part of application No. 15/984,172, filed on May 18, 2018, now Pat. No. 11,170,881.

(51) Int. Cl.
*G16H 10/40* (2018.01)
*G16H 50/30* (2018.01)

(56) References Cited

U.S. PATENT DOCUMENTS

| | | |
|---|---|---|
| 2009/0138318 A1 | 5/2009 | Hawkins et al. |
| 2014/0074454 A1 | 3/2014 | Brown et al. |
| 2014/0249830 A1 | 9/2014 | Gallopyn et al. |
| 2014/0249831 A1* | 9/2014 | Gallopyn ............... G16H 40/20 705/2 |
| 2016/0210434 A1* | 7/2016 | Al-Sharif ............... G16H 50/30 |
| 2016/0321414 A1* | 11/2016 | Salganicoff ........... G06N 20/00 |
| 2016/0371441 A1 | 12/2016 | Day et al. |
| 2017/0039336 A1 | 2/2017 | Bitran et al. |
| 2017/0140105 A1 | 5/2017 | Smith |
| 2017/0181645 A1* | 6/2017 | Mahalingam .......... G16H 10/60 |
| 2019/0324047 A1* | 10/2019 | Depraetere ...... G01N 35/00871 |

* cited by examiner

DEVICE AND METHODS FOR MACHINE LEARNING-DRIVEN DIAGNOSTIC TESTING

CROSS-REFERENCE TO RELATED APPLICATIONS

The present application is a divisional of U.S. Non-Provisional application Ser. No. 16/198,709, entitled "Device and Methods for Machine Learning-Driven Diagnostic Testing" filed on Nov. 21, 2018. U.S. Non-Provisional application Ser. No. 16/198,709 is a continuation-in-part of U.S. Non-Provisional application Ser. No. 15/984,172, entitled "Devices and Methods for a Healthcare Collaboration Space", and filed on May 18, 2018, now U.S. Pat. No. 11,170,881, issued on Nov. 9, 2021. The entire contents of the above-listed applications are hereby incorporated by reference for all purposes.

FIELD

Embodiments of the subject matter disclosed herein relate to a user interface for presenting information obtained from one or more machine learning models, and in particular, to a user interface for presenting diagnostic testing information.

BACKGROUND

Acute care of patients in a hospital or other medical facility may be carried out with multiple care providers per patient and may include multiple patient monitoring devices monitoring each patient. Thus, to ensure a rapid response should a patient's condition deteriorate, near-continuous monitoring of the output from the multiple monitoring devices may be necessary. Further, coordination of patient care among all the care providers may be complicated or time-consuming, further stretching care provider resources. Additionally, the separation between care providers and the laboratory conducting diagnostic and/or monitoring tests may lead to operational inefficiencies, such as the inability to reprioritize ordered diagnostic lab tests as a patient state changes.

BRIEF DESCRIPTION

In one embodiment, a method includes generating a patient-specific collaboration channel comprising a patient-specific dashboard and a communication thread between a care provider team monitoring a patient and a virtual healthcare assistant, storing, at the channel, text- and/or rich media-based messages on the communication thread between one or more care providers of the care provider team and the virtual healthcare assistant, at least a portion of the messages on the communication thread including patient-specific medical data, and responsive to a prompt, outputting at least a portion of the communication thread that includes the patient-specific medical data to a display device. It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 1:
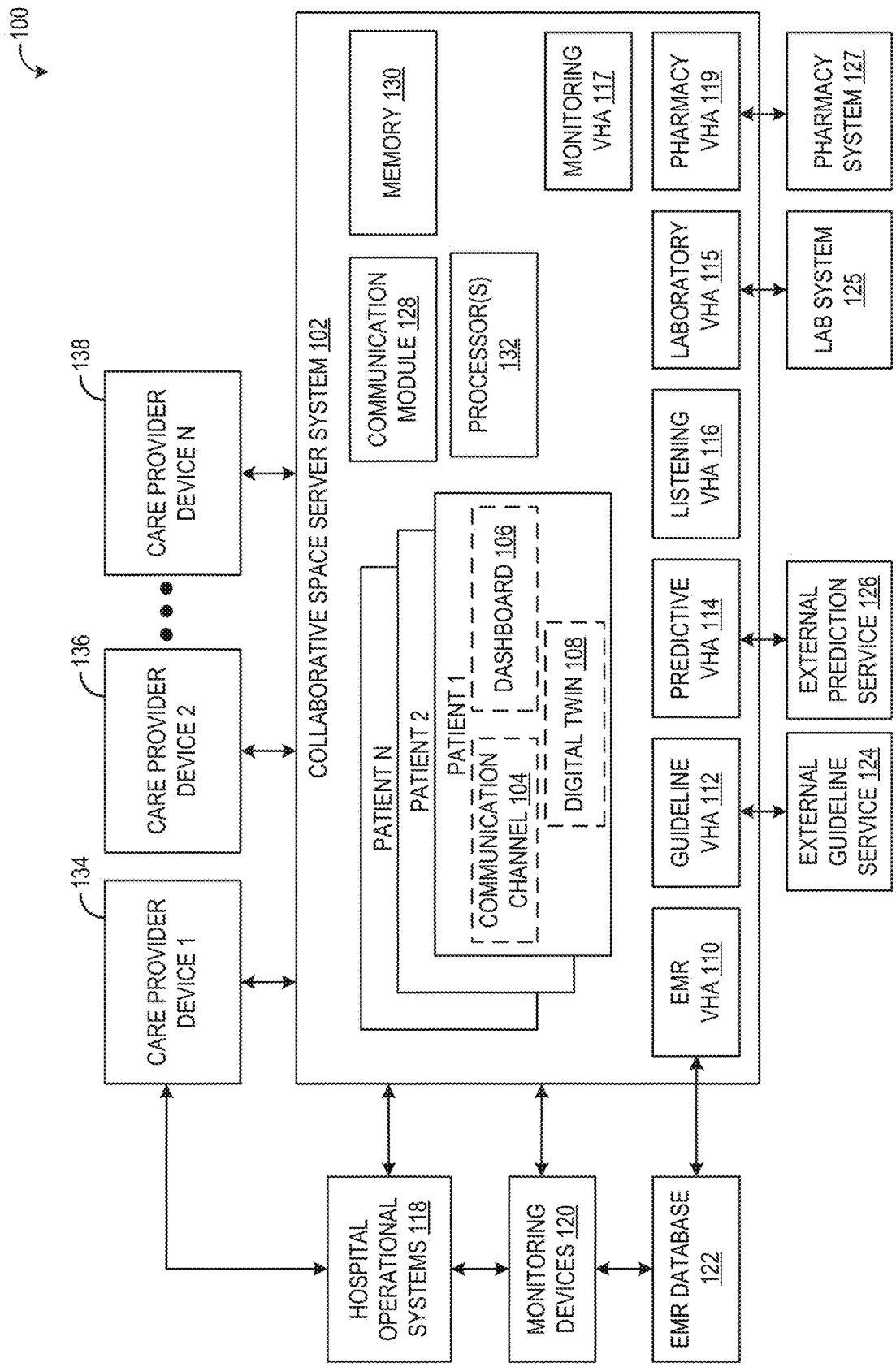
FIG. 1 schematically shows an example collaborative healthcare system.

The following description relates to various embodiments of a collaborative healthcare system that facilitates communication among care providers of a patient (which may be collectively referred to as a care provider team) and also utilizes machine and/or other deep learning models (e.g., in the form of virtual healthcare assistants) to perform certain patient monitoring and diagnostic activities. The collaborative healthcare system includes patient-specific communication channels that include communication thread-dashboard pairs to facilitate communication among the care providers and virtual healthcare assistants (also referred to as bots) on the communication thread while also graphically providing relevant patient care information (current vital signs, trends, medical history, diagnostic lab test information) to the care providers via the dashboard.

The virtual healthcare assistants may function as information retrievers, data monitors, predictors, and more to assist the care providers. The virtual healthcare assistants may provide requested patient data (e.g., fetch data from an electronic medical record), detect changes in patient state and alert the care providers of the changed state (e.g., by detecting that a patient vital sign has reached a condition relative to a threshold), and provide care guidelines, suggested diagnostic tests, and diagnoses to the care providers. The virtual healthcare assistants may be trained to communicate using natural language including medical language, thereby allowing for care providers to communicate with the virtual healthcare assistants in the same manner as other care providers.

Each communication channel may be specific to a given patient in a given acute care facility or other medical facility or healthcare setting (e.g., hospital, urgent care facility, or nursing home). A communication channel may be initiated upon admission of the patient to the medical facility. Each care provider of the patient may be joined to the communication channel, thereby allowing collaboration and communication among all care providers (e.g., doctors, nurses, and/or specialists such as radiologists) of the patient. The one or more virtual healthcare assistants may also be joined to the communication channel. Communication occurring on the communication channel may be in the form of text messages, rich media, and/or other forms, thereby allowing care providers to view graphs of patient medical trends, medical images, and so forth. Messages sent and received on the communication channel may be saved at a central location as a communication thread, allowing care providers to access prior conversations on the channel. For example, if a virtual healthcare assistant detects a change in a patient condition that indicates potential health issues, such as high blood pressure, the virtual healthcare assistant may note the high blood pressure and alert the care provider(s) via the communication thread. The blood pressure may be displayed via the patient dashboard along with the alert. A care provider may view the blood pressure measurement by selecting the alert in the communication thread. Later, the care provider may select a graphical display of the alert in the dashboard in order to launch the portion of the communication thread in which the blood pressure alert was issued.

The dashboard and communication thread may be viewable from a variety of client devices, including but not limited to a provider client device (such as a monitor in a nurse's station) and a provider mobile device (such as a tablet or smart phone). Thus, care providers may have access to relevant data and assistance from the virtual healthcare assistants from virtually any allowed location within the medical facility, and even off-site locations in some examples.

Further, the collaborative healthcare system described herein may facilitate communication and coordination among care providers, laboratory service providers, and/or pharmacists. In order to accurately diagnose a patient condition and/or monitor patient status, a care provider may order one or more lab tests, where a patient specimen is sent to an on-site or off-site laboratory and lab service providers at the laboratory analyze the specimen and send the results of the analysis back to the care provider. Once a patient condition is diagnosed, the condition may be treated via administration of one or more medications, which may be dispensed by a pharmacist at an on-site or an off-site pharmacy. To increase operational efficiency (e.g., by identifying duplicate lab test requests and/or missing lab test requests, by suggesting appropriate tests based on patient condition, by providing an estimated time of arrival of a test result or medication, or by reducing clinician calls to the lab or pharmacy to inquire about test or medication status), a care provider may communicate with a laboratory and/or pharmacy via a patient-specific communication channel, as described above, or via non-patient specific communication channel(s) between the care provider and lab or pharmacy. One or more of the virtual healthcare assistants may also assist in facilitating communication among the care providers, lab service providers, and/or pharmacists/technicians. For example, a virtual healthcare assistant may detect that a patient's state is deteriorating (e.g., based on patient medical data from one or more patient monitoring devices) and notify the lab service provider of the patient's state, which may result in the patient's lab test request being advanced (e.g., given higher priority) in a testing queue. Conversely, a virtual healthcare assistant may detect that a patient's lab test request is in the process of being fulfilled and the virtual healthcare assistant may notify the care giver(s) for that patient that the patient's test results may be expected within a threshold duration.

Figure 2A:
FIGS. 2A and 2B show an example display device displaying a communication thread occurring on a communication channel of the collaborative healthcare system.
Figure 2B:
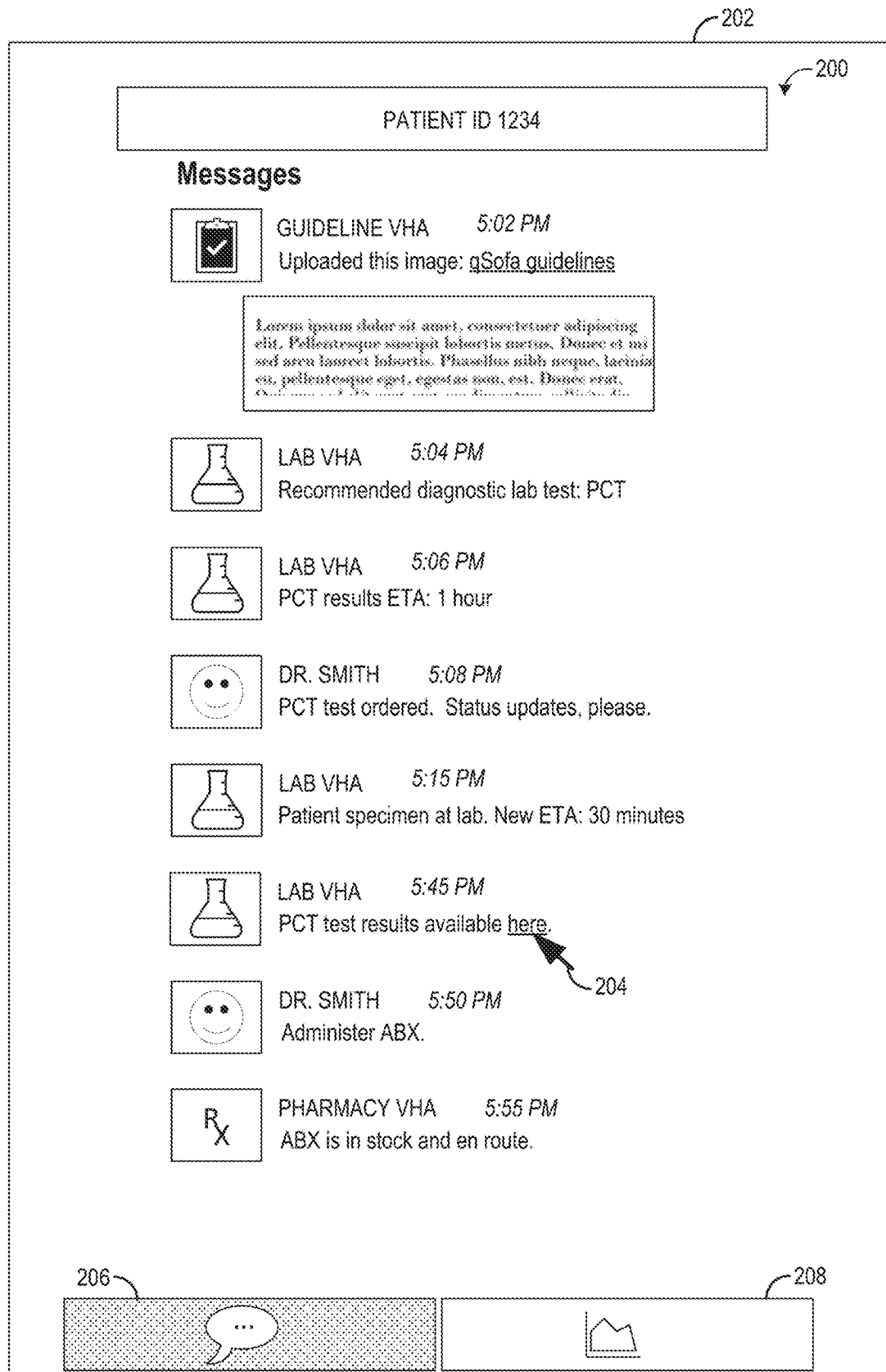
Figure 3:
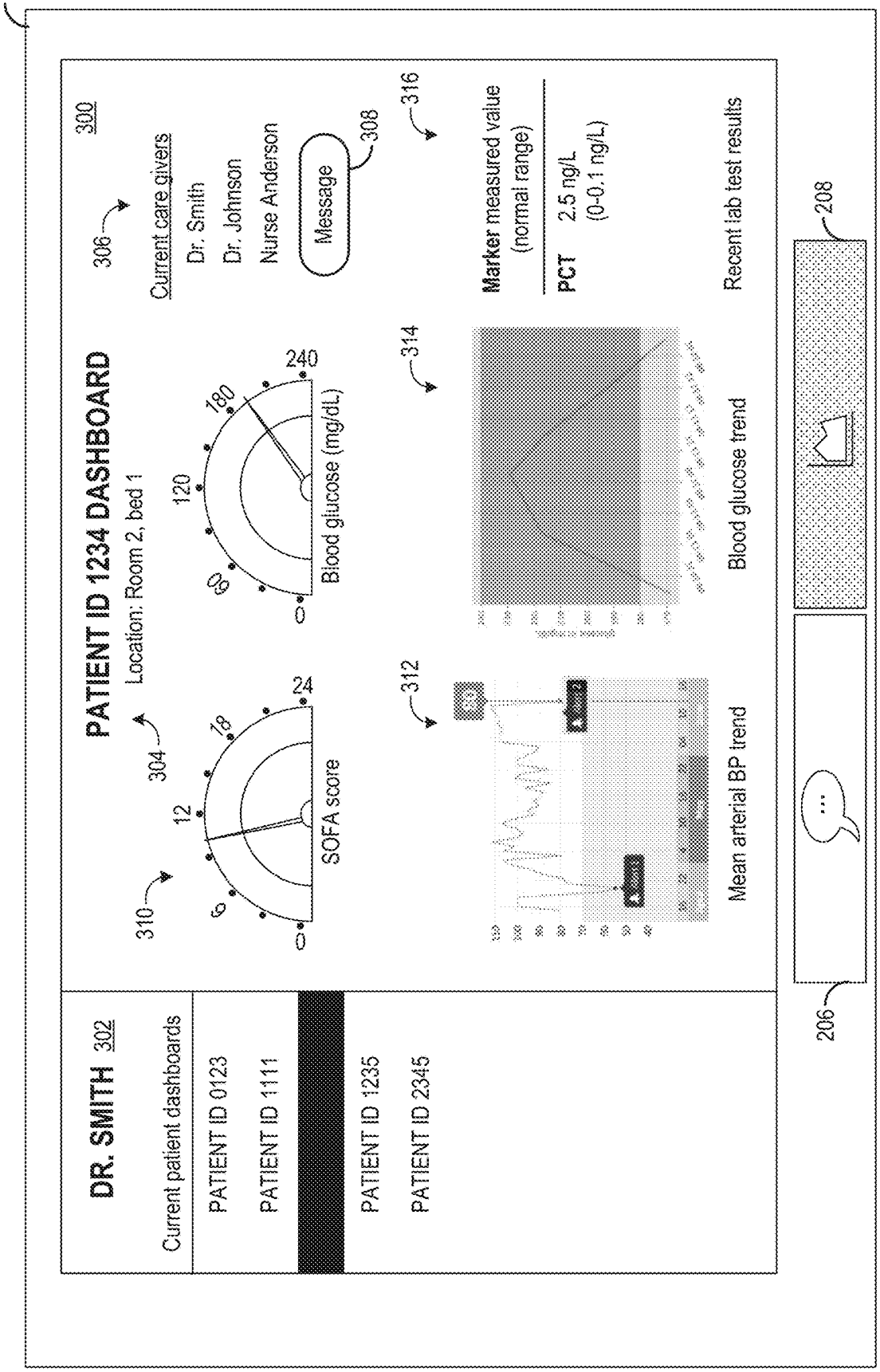
FIG. 3 shows an example display device displaying a dashboard of the collaborative healthcare system.
Figure 4:
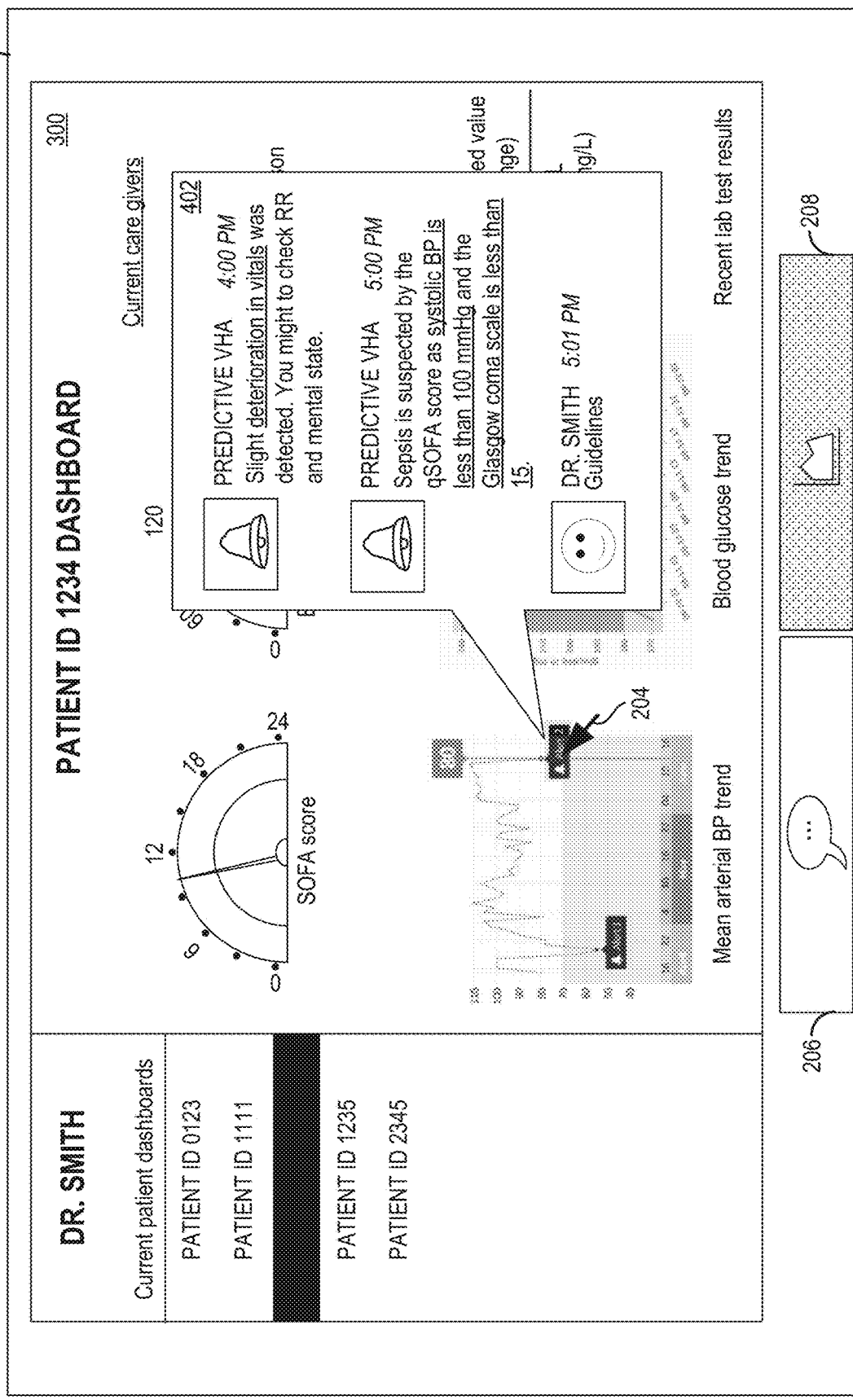
FIG. 4 shows an example display device displaying the dashboard of FIG. 3 including display of a portion of the communication thread of FIGS. 2A and 2B.
Figure 5:
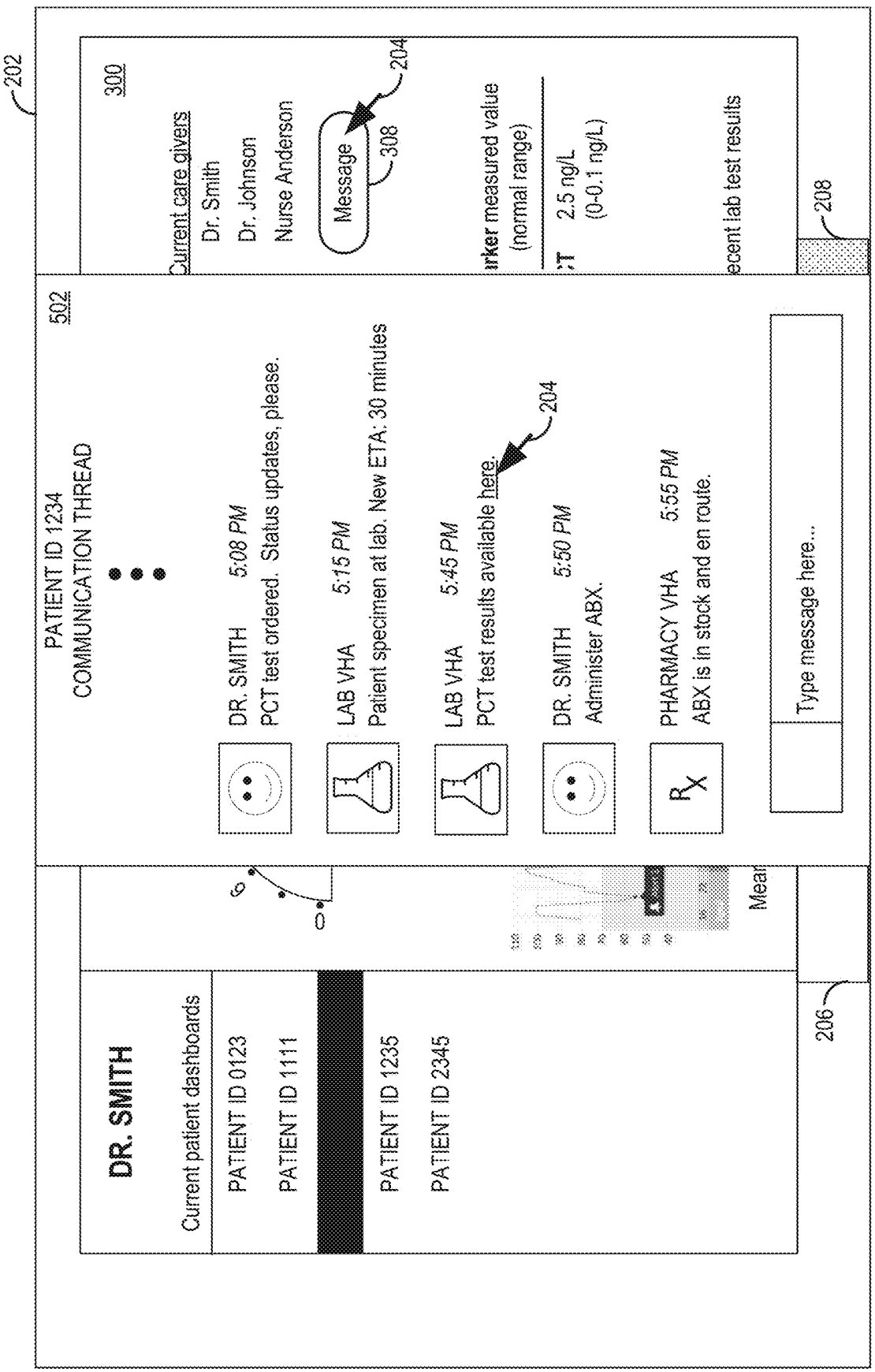
FIG. 5 shows an example display device displaying the dashboard of FIG. 3 including display of a full version of the communication thread of FIGS. 2A and 2B.
Figure 6:
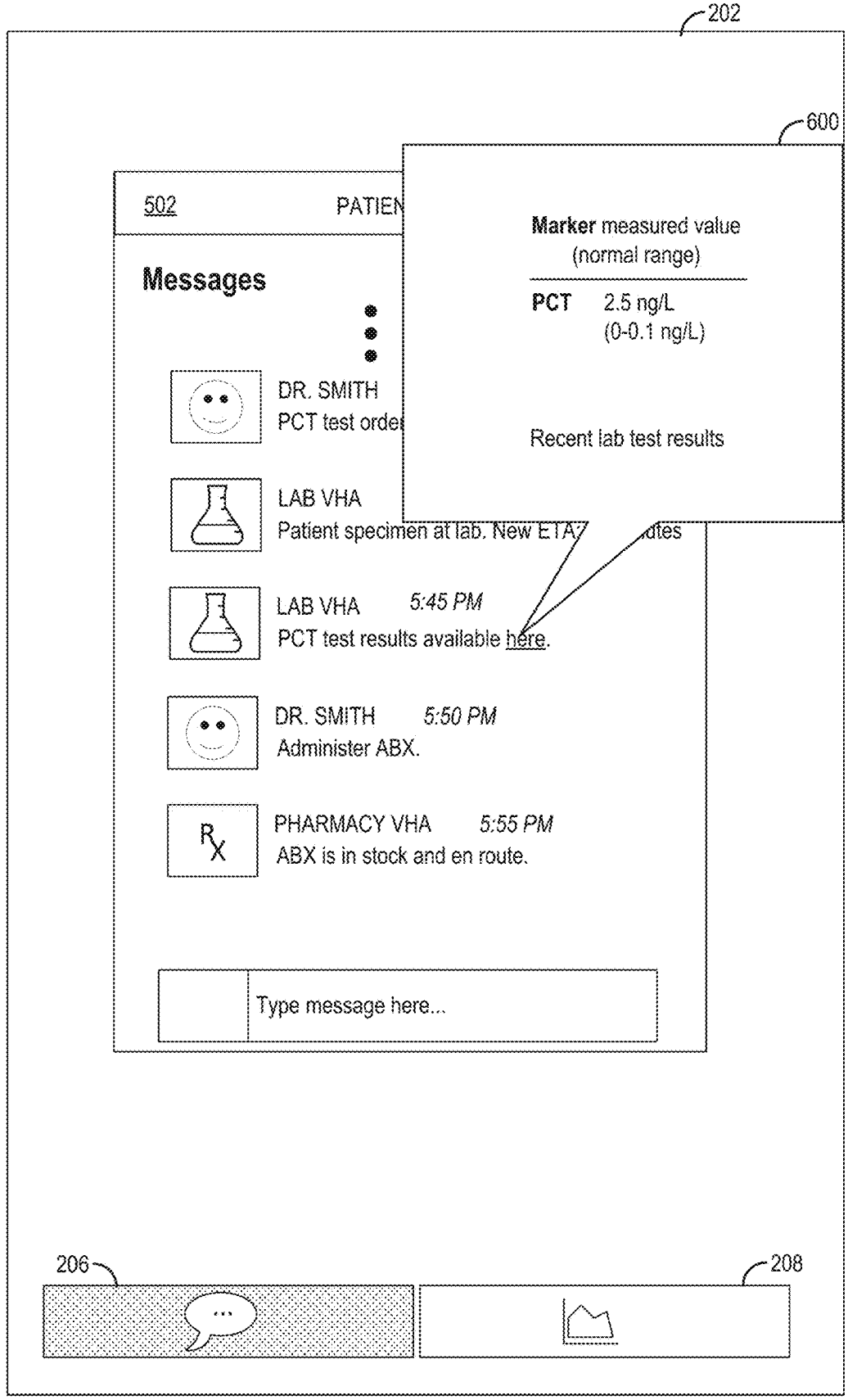
FIG. 6 shows an example display device displaying the communication thread of FIGS. 2A and 2B including display of a preview of the dashboard of FIG. 3.
Figure 10:
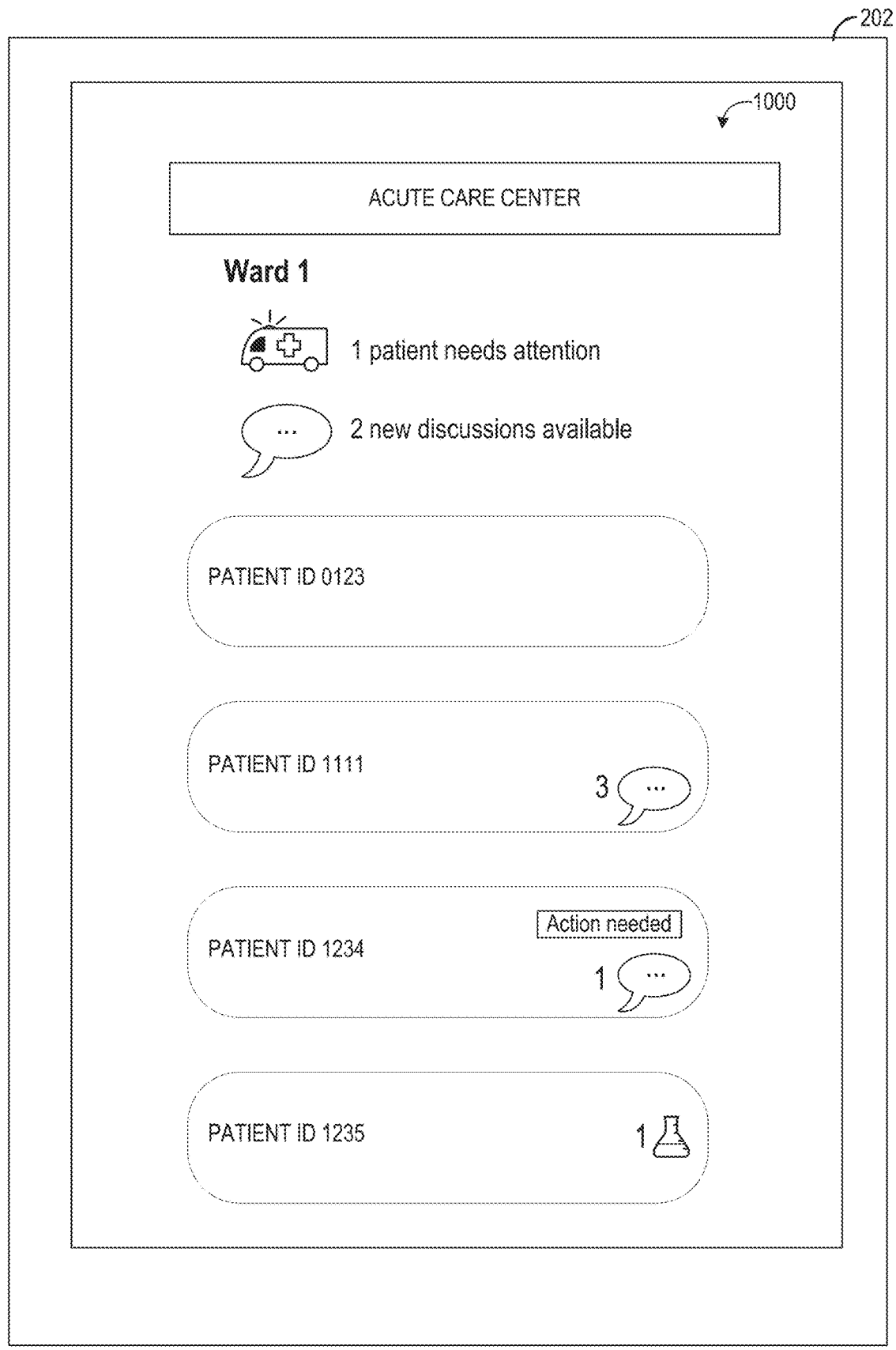
FIG. 10 shows an example display device displaying a collaborative interface.

An example collaborative healthcare system is shown in FIG. 1. The collaborative healthcare system may be included in or associated with a medical facility and may include a communication channel comprising a communication thread and a dashboard for each admitted patient of the medical facility. The collaborative healthcare system may further include one or more virtual healthcare assistants. Communication may occur on a communication channel in the form of a communication thread (e.g., of text and/or rich media messages) between care providers of the patient and the one or more virtual healthcare assistants, as shown in FIGS. 2A and 2B as well as FIG. 11. Patient-specific medical information may be displayed to the care providers and/or other users via a dashboard. As shown in FIGS. 3 and 12, the dashboard may be launched in response to a first selection of a link on the communication thread. The dashboard may be configured to display alerts output by the one or more virtual healthcare assistants, and the alerts may be selectable to launch a portion of the communication thread occurring on the communication channel, as shown in FIG. 4. The dashboard may be further configured to display a control button selectable to launch a full version of the communication thread, as shown in FIG. 5. As shown in FIG. 6, a preview of the dashboard may be launched in response to a second selection of a link on the communication thread. Further, a collaborative system interface, as shown in FIG. 10, may be displayed on a suitable display device in order to allow a user to select a communication channel or dashboard to view.

Figure 7:
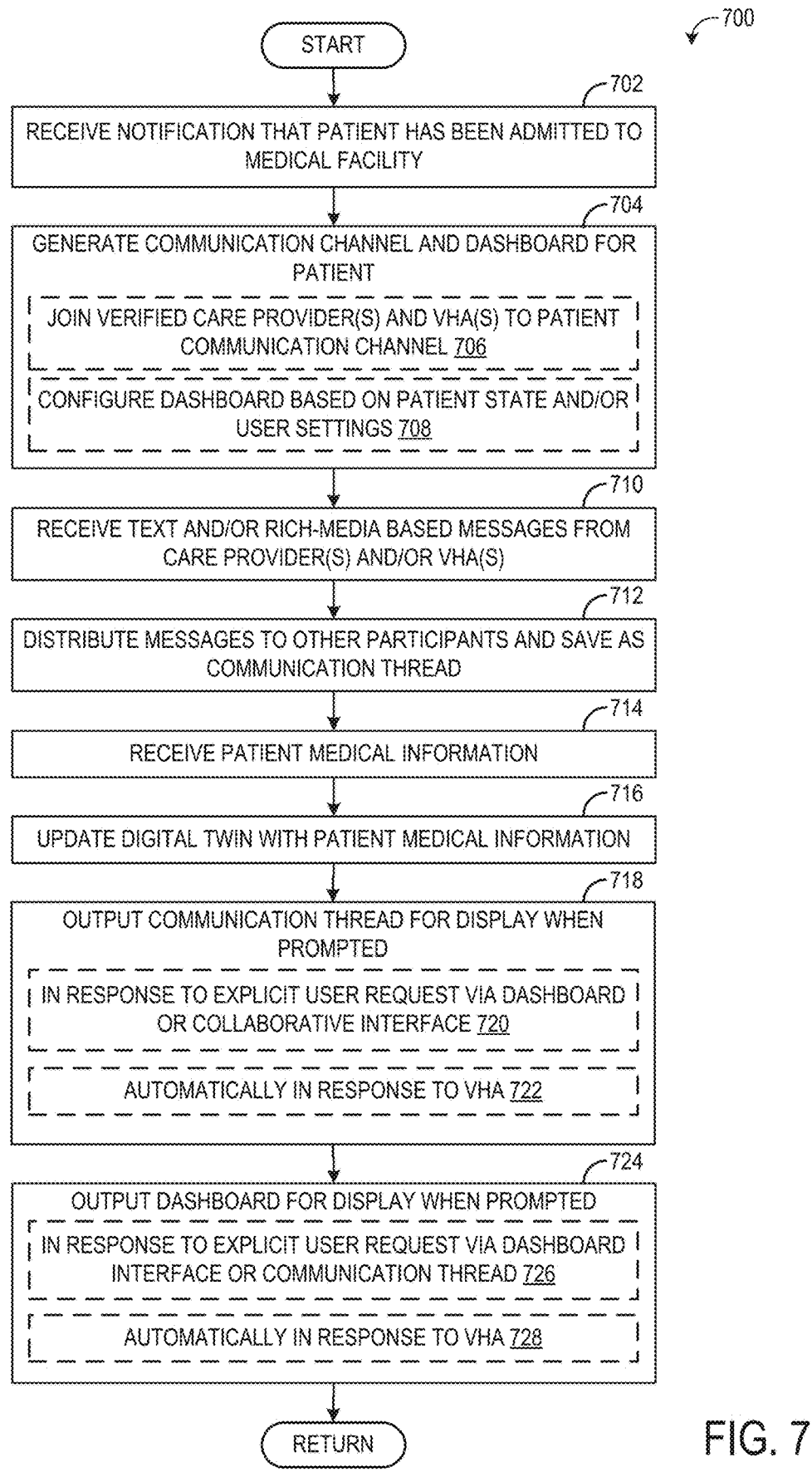
FIG. 7 is a flow chart illustrating an example method for facilitating communication within a collaborative healthcare system.
Figure 8:
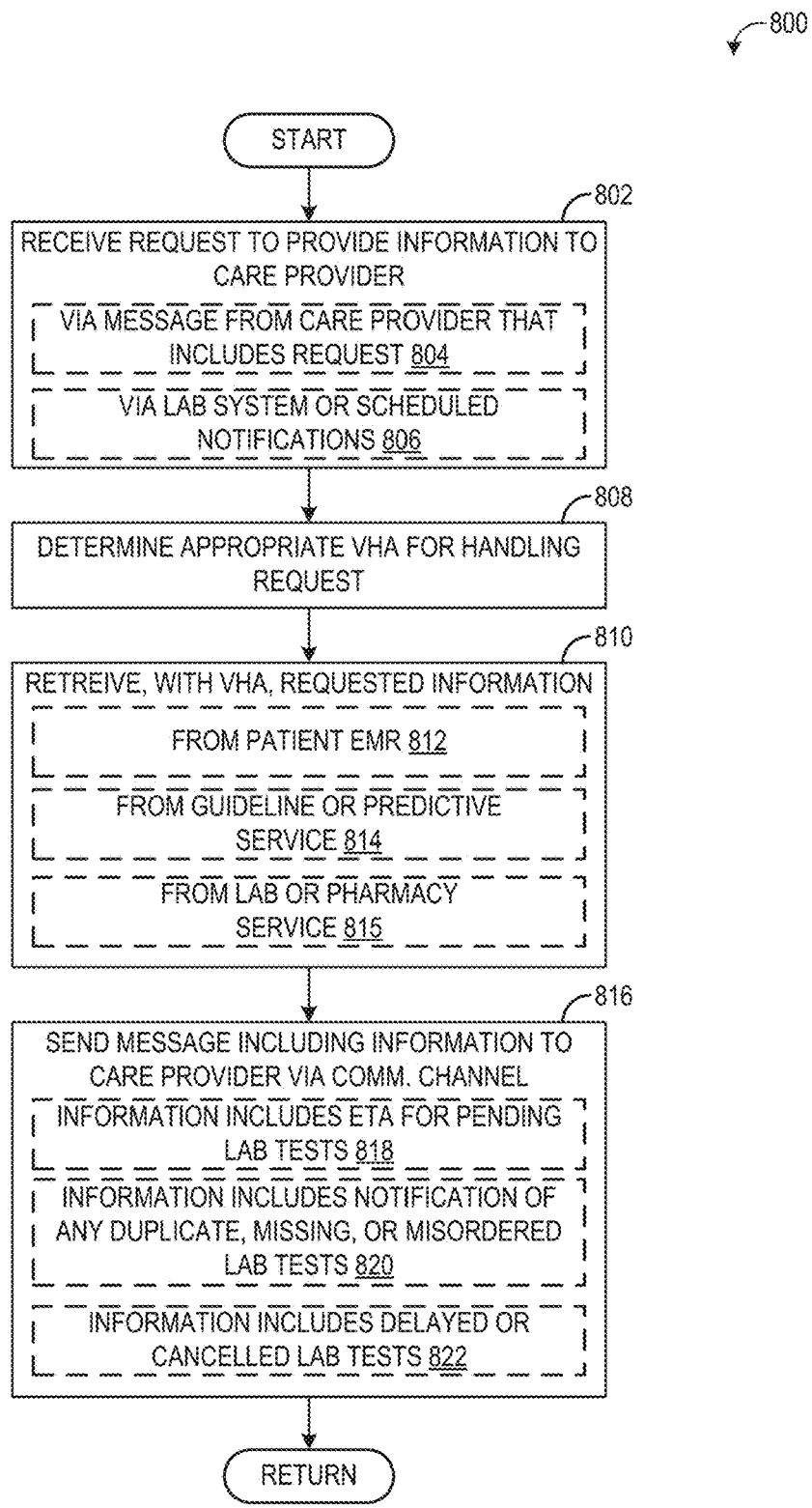
FIGS. 8 and 9 are flow charts illustrating example methods for one or more virtual healthcare assistants of the collaborative healthcare system.

The communication thread-dashboard pairs may be generated and accessed according to the method illustrated in FIG. 7. The virtual healthcare assistants may provide assistance to the care providers of the patient by retrieving medical information of the patient from an electronic medical record, providing treatment or care guidelines, providing predications of future patient states, and/or providing lab test notifications and tracking, as shown by the method of FIG. 8. The virtual healthcare assistants may also provide information to the care providers in the appropriate clinical context of the current patient state. The virtual healthcare assistants may further be configured to monitor the condition/state of the patient and notify the care providers if the virtual healthcare assistants determine the state or condition of the patient has changed, including notifying the care providers of possible diagnostic lab tests to aid in patient state diagnosis and/or escalating priority of any pending lab tests, as shown in the method illustrated in FIG. 9. The virtual healthcare assistants may further be configured to notify the pharmacy of changes in the patient state that would either reprioritize requests, discontinue requests, or suggest changes in requests.

FIG. 1 schematically shows an example collaborative healthcare system 100 that may be implemented in medical facility such as a hospital. Collaborative healthcare system 100 may include a collaborative space server system 102. Server system 102 may include resources (e.g., memory 130, processor(s) 132) that may be allocated to store and execute a communication thread, a dashboard, and a digital twin for each of a plurality of patients. For example, as shown in FIG. 1, a communication thread 104, dashboard 106, and digital twin 108 are stored on server system 102 for a first patient (patient 1); a plurality of additional communication threads, dashboards, and digital twins may be stored on server system 102, each corresponding to a respective patient (patient 2 up to patient N).

As explained above, the communication thread 104 may facilitate communication among a care provider team (which may include multiple care providers that are each providing care to the patient (e.g., patient 1)) as well as one or more virtual healthcare assistants (explained in more detail below). Messages sent on the communication thread 104 may be saved and may be accessible via the dashboard 106 (and the dashboard may be accessible via the communication thread). Further, the patient medical information, including medical history, current state, vital signs, and other information, may be entered to the digital twin 108, which may be used to gain situational awareness, clinical context, and medical history of the patient to facilitate predicted patient states, procurement of relevant treatment guidelines, patient state diagnoses, etc.

Communication occurring on communication thread 104 may be displayed on one or more suitable display devices associated with a respective care provider device and/or medical facility administration device. Likewise, dashboard 106 may be displayed on the one or more display devices. As shown in FIG. 1, a plurality of care provider devices, from a first care provider device 134, a second care provider device 136, and on up to an nth care provider device 138, may be communicatively coupled to server system 102. Each care provider device may include a processor, memory, communication module, user input device, display (e.g., screen or monitor), and/or other subsystems and may be in the form of a desktop computing device, a laptop computing device, a tablet, a smart phone, or other device. Each care provider device may be adapted to send and receive encrypted data and display medical information, including medical images in a suitable format such as digital imaging and communications in medicine (DICOM) or other standards. The care provider devices may be located locally at the medical facility (such as in a nurses station or in the room of a patient) and/or remotely from the medical facility (such as a care provider's mobile device).

When viewing communication thread 104 and/or dashboard 106 via a display of a care provider device, a care provider may enter input (e.g., via the user input device, which may include a keyboard, mouse, microphone, touch screen, stylus, or other device) that may be processed by the care provider device and sent to the server system 102. In examples where the user input is a message to be sent to other care providers and/or one or more virtual healthcare assistants, the message may be sent to the server system 102, where the message may be saved as part of the communication thread 104 and then the server system 102 may send the message to other verified participants on the communication channel (e.g., the other care providers and/or one or more virtual healthcare assistants that are joined to the communication channel). In examples where the user input is a selection of a link or user interface control button of the dashboard, the user input may trigger display of the communication thread, trigger progression to a desired state of the dashboard (e.g., trigger display of desired patient medical information), trigger updates to the configuration of the dashboard, or other actions.

The collaborative space server system 102 may be communicatively coupled to hospital operational systems 118. The hospital operational systems 118 may store and/or control a variety of hospital-, care provider-, and patient-related information, including but not limited to patient admission information (including date of admission and location of the patient within the medical facility), patient care protocols and workflows, and care provider information including which care providers are monitoring/treating which patients. Further, the hospital operational systems 118 may be communicatively coupled to a plurality of monitoring devices 120, an electronic medical records (EMR) database 122 (described in more detail below), and one or more of the care provider devices. The monitoring devices 120 may include traditional medical devices monitoring respective patients, such as pulse oximeters, heart rate monitors, blood glucose monitors, and ECGs, as well as microphones, cameras, and other devices. The monitoring devices 120 may send output directly to the server system 102 and/or may send output to the hospital operational systems 118, EMR database 122, and/or one or more care provider devices. For example, a plurality of monitoring devices monitoring patient 1 may be configured to send output to the server system 102 and the server system 102 may be configured to send some or all of the data output by the monitoring devices to a care provider device (care provider device 134). Further, in some examples, server system 102, hospital operational systems 118, and/or EMR database 122 may receive diagnostic imaging information obtained from one or more imaging modalities, such as ultrasound, CAT, MRI, X-ray, etc.

The hospital operational systems 118 may direct creation of and control access to each communication thread and dashboard. For example, when a patient is admitted, the hospital operational systems 118 may associate the patient with an identifier (e.g., an identification code) and notify the collaborative space server system 102 to generate a communication channel for that patient. When a care provider is assigned to assist in management/treatment of the patient, the hospital operational systems 118 may notify the collaborative space server system 102 to join that care provider to the patient's communication channel (the care provider may also be associated with an identifier which may be used to identify the care provider and appropriately distribute messages sent and received on the channel). In this way, the hospital operational systems 118 may control who has access to patient information. In some examples, hospital operational systems 118 and/or server system 102 may control levels of accessibility to patient information depending on location of a care provider device (e.g., devices located at the medical facility may have access to more patient information than devices located remotely from the medical facility). Additional information about the hospital operational systems 118 is presented below.

Collaborative space server system 102 may further store instructions for (e.g., in memory 130) and be configured to execute (e.g., via processor(s) 132) a plurality of virtual healthcare assistants (VHAs). As shown, collaborative space server system 102 includes an electronic medical record (EMR) VHA 110, a guideline VHA 112, a predictive VHA 114, a listening VHA 116, a monitoring VHA 117, a laboratory VHA 115, and a pharmacy VHA 119. The VHAs may be realized as several VHAs each for a different purpose, as described herein, various groups of VHAs (e.g., a the guideline VHA 112 and predictive VHA 114 may be combined into one VHA that is configured to both diagnose or predict patient state and output relevant guidelines), or as one overall VHA, which represents all the different attributes that will be hereby elaborated. All activations of VHAs by human care providers may be performed by using natural language including medical language, either by text or by voice.

EMR VHA 110 is configured to retrieve patient information from an electronic medical record database, such as EMR database 122, and present the retrieved data via the communication thread and/or dashboard. For example, a care provider may send a request to the EMR VHA 110, through the communication channel, for a particular piece of patient medical history saved in an EMR of the patient. The EMR VHA 110 may receive the request and determine, from the natural language of the text, that the piece of patient medical history has been requested. The EMR VHA 110 may obtain the piece of medical history from EMR database 122. The EMR VHA 110 may then send the piece of medical history to the care provider in the form of a message on the communication thread 104. In some examples where the requested piece of medical history is also saved in the digital twin 108, EMR VHA 110 may be configured to retrieve the medical history from the digital twin 108.

EMR database 122 may be an external database accessible by EMR VHA 110 via a secured hospital interface, or EMR database 122 may be a local database (e.g., housed on a device of the hospital). EMR database 122 may be a database stored in a mass storage device configured to communicate with secure channels (e.g., HTTPS and TLS), and store data in encrypted form. Further, the EMR mass storage device is configured to control access to patient electronic medical records such that only authorized healthcare providers may edit and access the electronic medical records. An EMR for a patient may include patient demographic information, family medical history, past medical history, lifestyle information, preexisting medical conditions, current medications, allergies, surgical history, past medical screenings and procedures, past hospitalizations and visits, etc.

Thus, the EMR VHA 110 serves as a connection to the EMR database. The EMR VHA may interpret questions by the human care providers regarding the patient and allows querying the EMR database for relevant information regarding the patient (e.g. "what was the average systolic blood pressure in the last four hours?" or "show me the trend of the O2 saturation"). Queries can implicitly relate to the patient's status or medical history. The EMR VHA 110 also allows EMR-generated alerts to be formatted and sent into the patient communication thread (in a configurable manner either by a "setting" option or by voice command, such as telling it, e.g., "don't show me this again"). The EMR VHA 110 may also serve as a drug safety alerting system (including allergies, drug-to-drug relations, etc.) and may be thus connected to a relevant medical knowledgebase.

Guideline VHA 112 is configured to retrieve relevant care guidelines from an external guideline service 124. Guideline VHA 112 may be prompted, via communication occurring on communication channel, to retrieve care guidelines. For example, a care provider may explicitly request care guidelines for a given condition, such as sepsis, on the communication thread and guideline VHA 112 may query external guideline service 124 in response to the explicit request. In other examples, guideline VHA 112 may determine implicitly that care guidelines for a given patient condition are being requested and/or may be helpful. For example, guideline VHA 112 may parse communication on the communication thread 104 (e.g., between one or more care providers and/or a suitable VHA) to determine that guidelines are being requested (e.g., rather than receiving an explicit request for the guidelines, guideline VHA 112 may determine that two care providers are discussing guidelines and may retrieve the guidelines without being requested to do so). In a further example, guideline VHA 112 may determine, from patient vital signs (e.g., output by the one or more monitoring devices 120), digital twin 108, and/or other sources that a patient may be undergoing a given condition (e.g., high heart rate) and may automatically obtain guidelines for treating the condition.

External guideline service 124 may be a remote service accessed via a network, or external guideline service 124 may be a local service executed on a computing device of the hospital. The care guidelines obtained from external guideline service 124 may be preconfigured by protocols and guidelines that are specific to the medical facility that the collaborative space server system 102 services. Further, external guideline service 124 may include differential diagnoses trees that guideline VHA 112 may access to determine potential diagnoses based on a patient condition or state.

For example, with regards to the patient's state and medical history as search terms, e.g., if a diabetic patient has a high sequential organ failure assessment (SOFA) score and high glucose levels, specific guidelines will be queried without additional query terms, or alternatively the external guideline service may be queried by specifying specific guidelines. In other words, the guideline VHA may enter specific search terms to the guideline service based on patient state and symptoms (e.g., diabetes, SOFA score of five, glucose level of 190 mg/dL) to obtain one or more potential diagnoses and/or guidelines, or the guideline VHA may specifically ask for guidelines for a given condition (e.g., sepsis). The guideline VHA may also serve as a source for generating reminders for treatments that are part of a care protocol or to keep track of what decision-driving tests have been completed and what are still needed to complete the protocol. A change in patient status may be a trigger for automatic notification of relevant guidelines. The guideline VHA may also be used to plan a trajectory for the patient, of both disease progression and a care path. A patient trajectory may be determined based on the combined trajectories of vital signs, laboratory test results or other data for that specific patient. In defining a patient trajectory, the guideline VHA may assist care providers to adjust care pathways or to stay the course and give early warning if the patient deviates from the planned trajectory.

Predictive VHA 114 is configured to retrieve predictions of future patient states from an external prediction service 126. Predictive VHA 114 may detect and issue alerts on relevant changes in the patient's state (e.g., small but worrying changes in vital signs, changes in qSOFA score). Predictive VHA 114 may also predict future events (e.g., a prediction of sepsis being developed in the coming four hours) by connecting to external prediction service 126. Predictive VHA 114 may query external prediction service 126 with search terms indicating current and/or past patient state (e.g., blood pressure trend, glucose level trend, etc.). If prediction service 126 outputs a possible future condition, the predictive VHA 114 may send an alert into the communication thread, as text, and may provide supplemental information regarding the alert. The predictive VHA 114 may also track the response of human care providers as reflected in the communication channel or in the EMR orders registry. The predictive VHA 114 may obtain patient data from the EMR and different online monitoring devices 120 (ECG, cameras, etc.) as represented in the digital twin.

Listening VHA 116 is configured to monitor communication on the communication channel 104 as well as actual human voice communication to obtain/infer various information related to the patient. In doing so, listening VHA 116 serves as a monitor, by listening to the events in the patient's surroundings including medical staff conversations and patient's input (from moaning to speech). The monitored conversations/inputs may be used to record the patient's status (for EMR/digital twin) or to infer clinician reasoning (e.g., the listening VHA may catch an order to prescribe a certain antibiotic by a doctor, and understand an infection is suspected). The listening VHA 116 may receive output from one or more microphones positioned in proximity to the patient, for example, in order to monitor the conversations and inputs.

Monitoring VHA 117 is configured to receive output from the monitoring devices 120 and may track a patient condition or state based on the received output. In some examples, monitoring VHA 117 may present the received data via the communication thread and/or dashboard. For example, a care provider may send a request to the monitoring VHA 117, through the communication channel, for a particular piece of patient monitoring data, such as current heart rate. The monitoring VHA 117 may receive the request and determine, from the natural language of the request, that the patient medical data has been requested. The monitoring VHA 117 may obtain the patient medical data from the relevant monitoring device of the monitoring devices 120. The monitoring VHA 117 may then send the medical data to the care provider in the form of a message on the communication thread 104. In some examples, monitoring VHA 117 may be configured to save the medical data at the digital twin 108. Further, medical data received by monitoring VHA 117 may be displayed via the dashboard. In some examples, monitoring VHA 117 may obtain patient medical data only in response to a request from a care provider. In other examples, additionally or alternatively, monitoring VHA 117 may obtain medical data from the monitoring devices 120 independently of care giver request, and may output requested medical data when a care giver requests the data and/or when the received medical data is detected (by the VHA) as being abnormal, having changed, or otherwise indicative of an urgent patient state. In some examples, monitoring VHA 117 may be configured to provide received medical data to predictive VHA 114 and/or guideline VHA 112 in order to predict a future patient state based on current patient medical data and/or retrieve relevant care guidelines based on current patient medical data.

Laboratory VHA 115 (referred to as lab VHA 115 herein) is configured to facilitate communication between care provider(s) and a lab system 125. Lab system 125 may include one or more computing devices associated with an on-site or off-site laboratory that performs lab tests on patient specimens sent to the lab by the care provider(s). The one or more computing devices may include resources (e.g., memory and processors) allocated to store and execute a laboratory information system (LIS). The LIS may manage various aspects of the laboratory procedures, such as managing/assisting with tagging of incoming specimens (e.g., with patient and care provider information, test(s) to be conducted on the specimen, and so forth), tracking specimens (e.g., in storage, being processed), generating reports of test results, and the like. Accordingly, the LIS may interface directly with various laboratory equipment, such as mass spectrometers, chromatographers, analyzers, etc., and thus may have knowledge of which specimens are currently being tested, the results of such tests, and the performance status of the various pieces of equipment. The LIS may also provide additional data which is not communicated to the EMR which may help determine or predict patient status. Additionally, the LIS may have understanding of which/how many specimens are in the lab awaiting testing, and expected wait times until those specimens are tested (which, for a given specimen that is to undergo a given test, may be based on an average testing time for that test, a number of specimens ahead of the specimen for that test, and/or additional factors such as laboratory staffing, reagent availability, etc.). The LIS may also provide a platform for laboratory service providers, such as lab technicians and managers, to communicate with care providers via the server system 102.

Lab VHA 115 may detect when a care provider has ordered a lab test (either explicitly based on knowledge of the actual order sent to the lab (e.g., as communicated by lab system 125) or implicitly based on hearing the care provider order the lab test or tell the patient or other medical staff about the lab test) and then subsequently track and/or manage the lab test. For example, lab VHA 115 may occasionally query lab system 125 to determine an estimated time until the lab test results are available, or lab system 125 may periodically push out estimated time notifications to lab VHA 115. Lab VHA 115 may then present the estimated time(s) to care provider(s) via a communication thread for that patient. Once the test results are available, the lab VHA 115 may notify the care provider(s) and/or display the results of the lab test via the communication thread.

Further, the guidelines obtained by the guideline VHA 112 may include suggested lab tests that could be performed on patient specimens (e.g., blood tests) to facilitate diagnosis of a patient condition, monitor patient status, determine if an administered treatment is working, and so forth. As explained above, the relevant guidelines for a given patient may be presented to the care provider(s) via the communication thread for that patient. In examples where the obtained guidelines include suggested lab tests, the suggested lab tests may be communicated with lab VHA 115. Lab VHA 115 may determine if the suggested lab tests have been administered for that patient recently or if the suggested lab tests are currently underway. If the suggested lab tests have been administered recently or if the suggested lab tests are currently underway, lab VHA 115 may notify the care provider(s) via the communication thread that the suggested lab tests have already been performed or that the suggested lab tests are currently underway, so that the care provider(s) does not request duplicate lab tests. If the suggested lab tests have not recently been performed or are not currently underway, lab VHA 115 may notify the care provider(s) via the communication thread that the lab tests should be ordered.

Further, lab VHA 115 may notify lab system 125 that the lab tests may be ordered in the near future, so that lab system 125 may allocate/schedule resources in anticipation of conducting the tests. In response to the notifications received from lab VHA 115, lab system 125 may communicate the notifications to lab service providers so that laboratory resources can be more proactively planned, including staffing, supplies, and future investment of additional equipment to increase capacity and reduce wait time. Additionally, as expected future demand of laboratory testing increases, more realistic turn-around times can be communicated from the lab system 125 to the care provider/care provider team, resulting in fewer calls to the laboratory staff and reduced frustration among the care provider team. Thus, lab system 125 may notify lab VHA 115 of an expected wait time until each test result is predicted to be available, and lab VHA 115 may communicate the expected wait time(s) to the care provider(s) via the communication thread. In this way, the care provider(s) may not only be informed of which lab tests are recommended, but also the care provider(s) may be informed of when the results of such lab tests would be expected. As one example, if a lab test has a relatively long wait time (e.g., 48 hours), the care provider may opt to begin a treatment without confirming patient diagnosis via the lab test, as the risk of delaying treatment may be too high. On the other hand, if a lab test has a relatively short time (e.g., one hour), the care provider may opt to wait until the test results are available before selecting and administering a treatment option. Thus, knowing the expected wait time of a lab test result may inform treatment and care option decision making.

The communication between the care providers, lab VHA, and lab system may provide further benefits. For example, based on information received from the lab system (e.g., the results of strain cultures of specimens obtained from patients at the medical facility), the lab VHA may determine that multiple patients at the medical facility are harboring antibiotic resistant strains of bacteria. The lab VHA may then inform the care providers, via the communication thread, so that alternate therapeutic approaches may be applied. Additionally or alternatively, the lab VHA may inform a pharmacy VHA (described in more detail below) of the antibiotic resistant strain, and the pharmacy VHA may inform a care provider/care provider team of the antibiotic resistant strain when a prescription is placed to treat a patient infected with that bacteria (e.g., the pharmacy VHA may determine that a care provider is about to place a prescription for antibiotic X for a patient and may output a notification into the communication thread for that patient notifying the care provider that an antibiotic X-resistant strain is currently infecting patients at the medical facility and suggesting an alternative, such as antibiotic Y).

Further, the lab system may send additional information regarding diagnostic lab tests that are not typically included the lab test results that are sent to the patient EMR, such as the physical properties of biological samples, morphological information, etc. By sending this additional information to the caregivers and the VHAs, the statistical properties of insights and predictions may be advanced.

Further still, in many cases the raw data communicated in the communication channel may be helpful to human care providers without interpretation or processing (e.g., a notification that simply indicates that a patient culture grew *C. difficile*). But other times, the assimilation of the raw data into the algorithms/models executed by and/or included as part of the VHAs may assist with prediction and treatment recommendations that may be the most helpful.

Predictive VHA 114 and/or monitoring VHA 117 may also communicate with lab VHA 115. For example, if monitoring VHA 117 detects a deterioration in a patient's state, monitoring VHA 117 may notify lab VHA 115 of the patient's deteriorated state. Lab VHA 115 may determine if that patient has any lab tests that have been ordered but not yet been fulfilled, and if the patient does have one or more lab tests that have been ordered but not fulfilled (e.g., the tests are waiting in a queue at the lab), lab VHA 115 may inform lab system 125 of the patient's deteriorated state and lab system 125 may adjust the position of that patient's specimen in any respective queues, so that the tests may be performed sooner, if possible. Additionally, if predictive VHA 114 provides a prediction for a future patient state, as explained above, the future patient state may be communicated to lab VHA 115, and lab VHA 115 may determine if any lab tests are pending or available that may expedite diagnosis of the patient state. Lab VHA 115 may then communicate the possible lab tests to the care provider(s) as well as inform lab system 125 of the pending or potential lab tests and/or notify lab system 125 of the predicted patient state. As one example, if sepsis for a patient is suspected and thus a procalcitonin (PCT) test for the patient is pending, and if predictive VHA 114 predicts that the sepsis may escalate in the next few hours, the priority of the patient's PCT test may be escalated/advanced so that the test may be performed as quickly as possible, preventing undue delay of the diagnosis and subsequent treatment of the sepsis. On the other hand, if predictive VHA 114 predicts that the sepsis patient may remain stable for the next few hours, the pending PCT test may be maintained at the current priority, which may allow other tests in line ahead of the patient's PCT test to be conducted.

In other embodiments, lab VHA 115 may manage the testing queues. For example, lab VHA 115 may have knowledge of each specimen that has been submitted to the laboratory for testing but that has not yet been tested. Lab VHA 115 may assign each pending specimen to a respective queue based on the laboratory equipment that will be used to analyze that specimen and/or based on a classification of the lab test that will be performed on that specimen. For example, all specimens that are to be tested using an enzyme-linked immunosorbent assay (ELISA) may be placed into a first queue, all specimens that are to be tested using a colorimeter may be placed into a second queue, etc. In another example, all specimens that are to undergo a blood panel lab test may be placed in a first queue, all specimens that are to undergo an antibody test may be placed in a second queue, etc.

Each pending specimen in a given queue may be given a priority ranking based on the date that the specimen was collected and/or the lab test was requested, the type of lab test being performed on that specimen (e.g., how time sensitive the test is, whether the test is being used to diagnose an urgent condition or a more benign condition), and/or patient information (e.g., whether or not the patient is relatively healthy, current diagnosed patient conditions). When resources are available to perform a given lab test (e.g., once a machine that performs a blood panel test is available), lab system 125 may send a request to lab VHA 115 asking which pending specimen should be analyzed next, and lab VHA 115 may send a message notifying lab system 125 of which pending specimen has the highest priority. Thus, if a patient state changes (e.g., a patient starts to deteriorate based on other patient parameters such as heart rate and respiration rate), lab VHA 115 may adjust the priority ranking for that patient's specimen so that the lab tests for that patient may be performed sooner, if possible.

In this way, the VHA(s) executing on server system 102 and/or lab system 125 may integrate data from the patient bedside with laboratory information systems to enable smart, automated prioritization and/or re-prioritization of pending queued patient test requests. The lab VHA and/or lab system 125 may evaluate the prioritization of queued lab samples (e.g., patient specimens) based on an algorithm which stratifies patients by a risk of deterioration. The algorithm may be based on values and/or trends of multiple patient parameters including but not limited to heart rate, respiratory rate, blood pressure, temperature, urine output, Glasgow Coma Score, early warning scores, etc. Deteriorating patients may trigger via the algorithm an escalation of priority for lab test requests that are queued relative to other patients' lab test requests which have not triggered escalation.

As an illustrative example, if a patient's respiratory rate increases, blood pressure decreases, urine output decreases, and the Glasgow coma score increases, then the patient's lactate test request would increase in priority in the lab's queued samples to be tested. Example patient lab test requests which could be escalated include but are not limited to lactate, procalcitonin, blood cultures, arterial blood gas (ABG), creatinine, etc. Once a patient has been identified as deteriorating, and the algorithm has indicated an increased risk score, then the care provider may be informed (e.g., by the lab VHA 115 via the communication thread) of any lab test requests which are now recommended/required by hospital protocol, but have not yet been requested.

As explained above, lab VHA 115 may track pending lab test requests as well as report test results when available. By tracking pending/completed lab tests, lab VHA 115 may inform a care provider about duplicate testing upon ordering, or a test that should be ordered but that has not been ordered (per hospital requirements) as a notification to the ordering care provider.

Lab VHA 115 may link test ordering with advanced analytics that provide the care provider with typical lab patterns as well as with guideline and hospital requirements. For example, if a patient presents with signs and symptoms of "x" disease for which there are diagnostic lab tests available, the guideline VHA may suggest the lab tests be performed, and the lab VHA may notify the care provider if that test has already been ordered (or if the result of that test is in the patient's EMR), or report what prior testing was performed and how the prior testing might affect whether or not the care provider places the order or suggests another test that is recommended based on standard guidelines and/or typical ordering patterns. The care provider may choose to disregard the information, or request additional information.

For example, the patient may have signs and symptoms of deterioration and the care provider may suspect that the patient might be a carrier for chronic hepatitis C, an infection that could complicate the hospitalized patient's situation and require care providers to be aware of the patient's infection. The care provider could order a HCV antibody screening test. However, if the care provider orders a HCV RNA molecular viral load test (which should occur as a reflex to an antibody test), the lab VHA 115 may alert the care provider, via the communication thread, about the wrong order sequence. If the antibody screening test is conducted and the results are positive, the lab VHA may alert the care provider and suggest ordering a reflex HCV RNA test (or if the hospital typically orders reflex testing, this could be automatic).

Lab VHA 115 and/or one or more other VHAs (e.g., predictive VHA 114, guideline VHA 112, and/or EMR VHA 110) may recommend lab tests that may be ordered for a given patient based on other patients with similar medical/health parameters as the patient and/or utilizing the patient's clinical, anthropometric, and demographic information. Machine learning models may be built based on the digital twin concept (parameters of patient information and modeling of care of patient data across patient populations) and algorithms may be developed that help predict and model patient status. Based on predicted outcomes, lab VHA 115 may generate lab test ordering suggestions to the care provider for consideration.

As an example, a care provider may be undecided what lab test(s) should be ordered to diagnose a patient that appears to be deteriorating. Lab VHA 115 may include a testing model that may be executed in response to a request from the care provider. The testing model that may use current patient parameters (e.g., current diagnosed conditions, vital signs, length of stay at the medical facility, recent travel history, demographic information, etc.) as inputs, and based on the inputs, the testing model may output suggestions for possible lab tests that should be ordered, which may be communicated to the care providers via the communication thread. In some examples, a digital representation of the health of the patient (e.g., digital twin 108) generated from obtained medical data of the patient may be used as an input to the model. For example, a subset or all of the medical data stored as part of the digital twin may be entered into the testing model.

The testing model may be a machine learning model or other deep learning model that is trained using information from past patients and known patient outcomes for those past patients. For example, the testing model may be trained with a plurality of training datasets, where each training dataset is specific to a respective patient and includes patient parameters for that patient and known outcomes for that patient. The patient parameters may include demographic information (e.g., age, sex, nationality, etc.) for that patient, current and/or past diagnosed conditions for that patient, patient lifestyle information (e.g., travel history, drug or alcohol use, exercise habits), current vital/health signs (e.g., blood pressure, heart rate, respiration rate, qSOFA score, Glasgow Coma score, alertness, etc.) for that patient, and so forth. The known patient outcomes may include, for each respective patient, what lab tests were performed on that patient. In some examples, the known patient outcomes (e.g., which lab tests were performed) may be classified by whether those lab tests led to a correct diagnosis of a patient condition.

For example, the patient may have signs of confusion and deterioration, and the care provider may suspect the patient has encephalitis (e.g., inflammation of the brain that might be caused by herpes simplex virus). The care provider may be unsure which lab tests would have the most likelihood of diagnosing the patient. Thus, the care provider may send a request to the lab VHA for a list of possible lab tests, via the communication thread for that patient. The lab VHA may enter relevant patient parameters into the testing model (e.g., patient vital signs, patient demographic and lifestyle information, as well as clinical suspicions such as encephalitis) and the testing model may output one or more possible lab tests that could be conducted to diagnose the patient, based on population wide information. In this case, if the patient had recently traveled to India, the patient's travel history may have been noted in the patient's EMR (e.g., based on patient conversation with a care provider and/or based on a prior appointment where the patient received vaccinations in anticipation of traveling to India). The testing model may then output suggested lab tests to test for Japanese Encephalitis Viral infection, as the testing model may have knowledge that India was recently experiencing an outbreak of Japanese Encephalitis Virus and therefore laboratory testing for this might be considered. If patient travel to India was not noted, the testing model may suggest a test for the most common cause of the encephalitis based on disease prevalence and international and/or hospital-specified guidelines.

Lab VHA 115 may facilitate direct access to an instrument used to process a patient specimen to generate a test result (e.g., lab VHA 115 may query the LIS or the testing instrument to determine which specimen is currently being processed and at what stage of processing that specimen is in), and calculations may be performed that would be used to predict an estimated time of arrival for a laboratory result. This may be accomplished by communication between lab VHA 115 and the LIS of lab system 125 or the testing instrument itself. If lab VHA 115 determines that a lab result is delayed or cancelled, the lab VHA 115 may notify a care provider via the communication thread for that patient, so that the care provider may be informed in real-time of the test status. In some examples, if the lab test has been cancelled, lab VHA 115 may inform the care provider of the reason why the lab test was cancelled, and/or whether a new patient specimen needs to obtained, or if the care provider needs to send a re-order request for the same (previous) specimen for another test. An estimated time of arrival for a lab test result may be determined based on average sample arrival times and predictions made by instrumentations (typically sample to result timing) which would be calculated automatically. Further, reasons for sample failure (clotting, instrument crash, etc.) may be sent to notify the care provider. Further, lab VHA 115 may notify a care provider when an incorrect order was placed, e.g. a care provider orders a sample collected in wrong tube, wrong test for indication, etc.

For example, a care provider may order a procalcitonin (PCT) test for a patient thought to have sepsis due to bacteremia. The lab VHA 115 may automatically calculate the estimated timing of the result and present the estimated time to the care provider, and in some examples may determine whether the care provider would like to receive updates on the status of the lab test. If the status of the lab test changes because the instrument that is processing/testing the specimen crashes (and thus loses all samples for that run), lab VHA 115 may be informed of the instrument crashing and may notify the care provider in real-time that the lab result is delayed and the reason for the delay. The care provider can decide what to do or consult the lab in real-time. For example, the care provider may decide to order another test on the blood sample of the patient that was already drawn. If the prior blood sample cannot be found or if the prior blood sample is corrupted (e.g., clotted), lab VHA 115 may notify the care provider and may also notify one or more lab service providers via lab system 125. The lab service provider and care provider may then engage in a chat over the communication thread to determine subsequent steps. If the care provider decides to order another specimen to be collected, the lab service provider may agree to run the specimen ahead of any new samples that arrive. The new ETA for the new lab test is automatically calculated and confirmed after the specimen is collected (e.g., blood is drawn) and again when the specimen enters the lab (e.g., in both instances, the bar code on the specimen may be is read). Another update may occur when the sample begins processing on the instrument. The care provider may check his/her device to see when the sample is expected, for example.

Likewise, the guidelines obtained by the guideline VHA 112 may include suggested treatment options that may be administered to a given patient. In addition to notifying the care provider(s) of the possible treatment options via the communication thread for that patient, the guideline VHA 112 may communicate the suggested treatment options with a pharmacy VHA 119. Similar to the lab VHA 115, the pharmacy VHA 119 may confirm whether or not the patient is already receiving the suggested treatment options and/or whether the patient is currently receiving treatment options which may interact with the suggested treatment options and communicate that information to the care provider(s) via the communication thread. Further, the pharmacy VHA 119 may communicate with a pharmacy system 127 that includes one or more computing devices associated with an on-site or off-site pharmacy that fills prescriptions as ordered by the care provider(s). The one or more computing devices may include resources (e.g., memory and processors) allocated to receive prescription requests and communicate the requests with pharmacy staff, track prescription fill status, notify an ordering care provider when a prescription is available, and so forth. The pharmacy VHA 119 may notify the pharmacy system 127 that prescriptions for the treatment options may be ordered, so that the pharmacy system 127 may notify staff and/or allocate/schedule resources in anticipation of filling the prescriptions. In response, the pharmacy system 127 may notify the pharmacy VHA 119 of an expected wait time until each prescription can be filled, and the pharmacy VHA 119 may communicate the expected wait time(s) to the care provider(s) via the communication thread. For example, if a treatment option includes a rarely-administered drug, the pharmacy system 127 may determine that the pharmacy does not have adequate stock on hand to fill the prescription. By notifying the care provider of the expected wait time, the care provider may consider alternative treatment options if the wait time is longer than desired.

The pharmacy can use the physician ordering patterns to measure the usage (and duration) of specific antibiotics as part of an antibiotic stewardship program. These ordering patterns, combined with what is known about local hospital acquired infections (and antibiogram data, if available) can be provided to the pharmacy system 127 by the pharmacy VHA 119, along with recommendations, allowing the pharmacist and/or infectious disease physician to evaluate the information as it becomes available in the context of other relevant findings reported real-time.

The pharmacist and/or infectious disease physician can either review and approve the pharmacy VHA recommendation, or make an alternative antibiotic prescription recommendation to the care team (either of which may be handled via the communication channel). Similarly, the pharmacy VHA can also suggest to the care team to consider discontinuing antibiotic treatment. For example, in the case where a specific FDA-approved lab result has discontinuation of antibiotic treatment within the test labeling (e.g. PCT results reach a certain level), or the collection of clinical findings suggest discontinuation of antibiotic treatment will improve outcome and/or treatment is no longer of benefit, the pharmacy VHA can provide a recommendation accordingly.

In further examples, the pharmacy system 127 may monitor clinician ordering patterns, dosage, duration, and trends. The pharmacy system 127 may also identify which patients are receiving IV medications outside the recommended dose limits as defined in the facility drug library, and contact the patient's care team to determine if the dose is intended or in error, and the pharmacy system 127 may receive related information from the pharmacy VHA. The pharmacy system 127 may also access data on the frequency of inappropriate administration of drugs (antibiotics, vaso-actives, etc.) and suggest training for the medical facility unit or individual care providers. The pharmacy system 127 may also access data from the pharmacy VHA 119 on short half-life drugs that are currently being administered (e.g., infused) and which are nearly depleted and then notify the pharmacy service providers and/or medical facility care providers so that the pharmacy can prepare a new container of the IV solution prior to the current container running empty. This would prevent likely adverse events as many of these drugs are vaso-active and require continuous administration to stabilize a hemodynamically unstable patient.

The VHAs may be configured to receive messages from human care providers and utilize natural language processing to determine what information is being conveyed in the messages. For example, the VHAs may utilize natural language processing to determine if a message received on the communication channel includes a request for patient medical information, and if so, determine what medical information is being requested. The VHAs may also be configured to process medical information of the patient (e.g., vital signs, medical history, current symptoms) received from the patient EMR, the monitoring devices, the care providers, and/or other sources and determine which parameters of the medical information may be used (e.g., entered into the guideline or prediction service) to determine a patient state (such as determine the likelihood the patient is experiencing a certain condition, such as sepsis). The VHAs may execute deep learning models (e.g., machine learning or other deep learning models such as neural networking) that are trained to understand medical terminology. Further, the deep learning models may be configured to learn updates or modifications to the models in an ongoing manner in a patient and/or care provider specific manner. For example, a predictive VHA may execute a deep learning model that is trained to determine that low blood pressure may be a symptom of relevance that should be entered into a prediction service or diagnosis tree, but then may be trained for a specific patient that low blood pressure for that patient is benign and may have less relevance.

The models may be trained in a suitable manner. In a first example, the models may be rule-based assistants that are configured with a set of answers for predetermined, likely questions. When a VHA receives a question, the VHA may be configured to output an answer from the set of answers. In a second example, the models may include directed acyclic graphs (DAG) of states, each of which include rules for how to react and how to proceed to various questions. However, such VHAs may only be configured to respond when there is a clear indication of the user intent (e.g., the user presses on a button "obtain heart rate") and entities (answer to "please provide the patient's date of birth" with a date).

Thus, the VHAs described herein may include artificial intelligence and be adapted to handle natural language which is a way to take human input and map it to intent and entities. The VHAs may be adapted to hold a state and map the state with (intent, entities) to an actionable API. The mapping may be performed by teaching machine learning models by providing the models with examples of such mappings. If a VHA is autonomous, the VHA may include a prediction or other mechanism that may trigger the VHA to initiate communication. The VHAs may also be configured to vary their reactions to make the VHAs more human like (this may also be performed by providing examples to a machine learning training algorithm).

Further, the training mechanism utilized may be specific for different VHAs. For example, the listening VHA (and the natural language processing engines of the other VHAs) may execute deep networks trained for natural language with medical language. This may be combined with taxonomies from the medical domain. The EMR VHA and the guideline VHA may receive the output (intent and entities) from the listening VHA and/or the respective natural language processing engine and map the output to queries. The VHAs may be trained by having examples of the best results of existing queries. The predictive VHA may be trained on its own clinical task. For example, if the predictive VHA is to predict if a patient will survive early release from an intensive care unit, then the predictive VHA may be trained on data of patients that were in the ICU and were released at different stages.

Additional VHAs may be included on the server system, such as VHAs specific to a patient state. Such an example may include a sepsis VHA that may only be joined to a patient communication channel when that patient is undergoing or at risk of developing sepsis. The sepsis VHA may be trained to specifically predict sepsis, obtain treatment guidelines for sepsis, suggest optimal lab tests to diagnose sepsis and/or monitor sepsis progression, and/or suggest treatment options for sepsis. Other VHAs may include a patient comfort VHA (e.g., a VHA configured to detect or predict patient pain, discomfort, hunger, or other symptoms not necessarily indicative of a particular medical condition but which care providers may want to be notified of to improve patient comfort), a communication VHA (e.g., that parses communication from care givers and facilitates sharing of information among the VHAs), and/or other VHAs. Further, various configurations of VHAs not disclosed above are within the scope of this disclosure, such as related VHAs being grouped into a single VHA (e.g., the monitoring and EMR VHAs being combined as one medical data VHR). For example, a single VHA may be trained for all of the above-described VHA possible skills.

A global view of multiple or all patient communication thread-dashboard pairs may be provided via to one or more of the care provider devices and the hospital operational systems 118. For example, the choice of the specific thread/dashboard pair to access may be controlled by an access application executing on collaborative space server system 102 that allows to a user to view all the relevant patients (for example, communication thread-dashboard pairs for all the patients being treated/monitored in a nurses station may be accessed on a workstation at the nurses station, or communication thread-dashboard pairs for all the patients being treated/monitored by a given care provider may accessed by that care provider on his or her mobile device). In some examples, alerts and important events within all the relevant communication channels will be signified in the global view. The choice to go into a specific communication channel may be made by a user picking the patient in the global view (or by an explicit voice command), but may be also be automated using automatic mechanisms which may detect the position of the care provider in respect to a patient (such as via BLUETOOTH® when entering a patient's proximity or based the context of a detected discussion).

The access application may allow export of only specific widgets (such as the blood pressure graph of a patient) of a communication thread and/or dashboard, or may allow more compound parts (such as a patient dashboard or a portion of the thread) to selected external applications and/or devices. For example, as explained above, devices located off-site of the medical facility may only be allowed access to some of the patient medical data, and the access application may control which patient medical data is viewable outside of the medical facility.

A management application executed on hospital operational systems 118 and/or collaborative space server system 102 may allow an administrator to update the care team that has access to a patient's communications channel, as described above. The management application may include an interface for configuring hospital specific protocols and care guidelines. The management application may also aggregate information from the communication channels to be used to predict needs for hospital operations, presenting forecasts for capital, disposable, and human assets based on aggregate acuity or disease statistics. Moreover, analytics of the information on the communication channel may be employed to improve the system and its predictors.

Collaborative space server system 102 includes a communication module 128, memory 130, and processor(s) 132 to store and execute the communication channel-dashboard pairs, digital twins, and VHAs, as well as send and receive communications, graphical user interfaces, medical data, and other information.

Communication module 128 facilitates transmission of electronic data within and/or among one or more systems. Communication via communication module 128 can be implemented using one or more protocols. In some examples, communication via communication module 128 occurs according to one or more standards (e.g., Digital Imaging and Communications in Medicine (DICOM), Health Level Seven (HL7), ANSI X12N, etc.). Communication module 128 can be a wired interface (e.g., a data bus, a Universal Serial Bus (USB) connection, etc.) and/or a wireless interface (e.g., radio frequency, infrared, near field communication (NFC), etc.). For example, communication module 128 may communicate via wired local area network (LAN), wireless LAN, wide area network (WAN), etc. using any past, present, or future communication protocol (e.g., BLUETOOTH™, USB 2.0, USB 3.0, etc.).

Memory 130 one or more data storage structures, such as optical memory devices, magnetic memory devices, or solid-state memory devices, for storing programs and routines executed by processor(s) 132 to carry out various functionalities disclosed herein. Memory 130 may include any desired type of volatile and/or non-volatile memory such as, for example, static random access memory (SRAM), dynamic random access memory (DRAM), flash memory, read-only memory (ROM), etc. Processor(s) 132 may be any suitable processor, processing unit, or microprocessor, for example. Processor(s) 132 may be a multi-processor system, and, thus, may include one or more additional processors that are identical or similar to each other and that are communicatively coupled via an interconnection bus.

As used herein, the terms "sensor," "system," "unit," or "module" may include a hardware and/or software system that operates to perform one or more functions. For example, a sensor, module, unit, or system may include a computer processor, controller, or other logic-based device that performs operations based on instructions stored on a tangible and non-transitory computer readable storage medium, such as a computer memory. Alternatively, a sensor, module, unit, or system may include a hard-wired device that performs operations based on hard-wired logic of the device. Various modules or units shown in the attached figures may represent the hardware that operates based on software or hard-wired instructions, the software that directs hardware to perform the operations, or a combination thereof.

"Systems," "units," "sensors," or "modules" may include or represent hardware and associated instructions (e.g., software stored on a tangible and non-transitory computer readable storage medium, such as a computer hard drive, ROM, RAM, or the like) that perform one or more operations described herein. The hardware may include electronic circuits that include and/or are connected to one or more logic-based devices, such as microprocessors, processors, controllers, or the like. These devices may be off-the-shelf devices that are appropriately programmed or instructed to perform operations described herein from the instructions described above. Additionally or alternatively, one or more of these devices may be hard-wired with logic circuits to perform these operations.

One or more of the devices described herein may be implemented over a cloud or other computer network. For example, server system 102 is shown in FIG. 1 as constituting a single entity, but it is to be understood that server system 102 may be distributed across multiple devices, such as across multiple servers.

While not specifically shown in FIG. 1, additional devices described herein (care provider device 134, care provider device 136, and care provider device 138, hospital operational systems 118, monitoring devices 120, EMR database 122, external guideline service 124, external prediction service 126, lab system 125, pharmacy system 127) may likewise include user input devices, memory, processors, and communication modules/interfaces similar to communication module 128, memory 130, and processor(s) 132 described above, and thus the description of communication module 128, memory 130, and processor(s) 132 likewise applies to the other devices described herein. As an example, the care provider devices (e.g., care provider device 134) may store user interface templates in memory that include placeholders for relevant information stored on server system 102. For example, care provider device 134 may store a user interface template for a patient dashboard that a user of care provider device 134 may configure with placeholders for desired patient information. When the dashboard is displayed on the care provider device, the relevant patient information may be retrieved from server system 102 and inserted in the placeholders. The patient information may include current patient vital signs, VHA alerts, desired patient state trends, or other information, as explained in more detail below. The user input devices may include keyboards, mice, touch screens, microphones, or other suitable devices.

FIGS. 2A-2B show an example communication thread 200 of a patient-specific communication channel, and as such may be a non-limiting example of communication thread 104. Communication thread 200 may be displayed on a display device 202. Display device 202 may include a screen on which the communication thread is displayed and may be coupled to and/or included as a part of a computing device, such as care provider device 134. Communication thread 200 may be displayed in response to a user request to display the communication thread. For example, the user (e.g., a care provider) may access a collaborative system interface that includes a global view of all communication threads and dashboards the user is authenticated to participate in (which may include all patients at the medical facility the care provider is attending to) and may select a desired communication thread to view. An example collaborative system interface 1000 is shown in FIG. 10. Collaborative system interface 1000 may be displayed on display device 202 or other suitable device and may include all patients admitted to a specific unit or ward of a medical facility. As shown, collaborative system interface 1000 includes identifying information specifying the medical facility ("acute care center") and relevant unit ("ward 1") of the medical facility, and further includes links to patient-specific communication threads and dashboards for the patients in that unit of that medical facility. However, in other examples, the patients shown via collaborative system interface 1000 may specific to a certain care provider.

Collaborative system interface 1000 may include a notification section whereby the user viewing collaborative system interface 1000 may be notified of urgent patient conditions, active communication channel discussions, lab test results, and other information. For example, collaborative system interface 1000 includes a notification section that shows that one patient requires attention (e.g., due to deteriorating vital signs) while two new discussions are available.

Collaborative system interface 1000 further includes links to patient communication thread-dashboard pairs. For example, FIG. 10 shows links to communication thread-dashboard pairs for patient ID 0123, patient ID 1111, patient ID 1234, and patient ID 1235. As explained above, each patient may be assigned an identifier that may be used to identify the patient on the communication thread and dashboard. In other examples, other mechanisms for identifying the patient may be used, such as location (e.g., bed 2 in room 4) or actual patient name. Additional patient links may be viewed by scrolling the interface. Each patient link may include notifications where relevant. For example, the link for patient ID 1111 includes a notification that three new messages are available to be viewed on the communication channel for that patient. The link for patient ID 1234 includes a notification that action is needed (e.g., due to high blood pressure or other significant vital sign being detected, which will be explained in more detail below) as well as a notification that one new message is available on the communication channel for that patient. In some examples, when a lab test result for a patient is available, the link for that patient may include a notification of an available lab test result, such as the notification displayed in the link for patient ID 1235. In examples, care providers may be notified of available lab test results through the communication channel for the patient, and thus the notification may include a notification that a new message is available.

Selection of a patient link may launch the communication thread or dashboard for that patient. For example, selection of the link for patient ID 1234 may launch the communication thread 200 for patient ID 1234, shown in FIGS. 2A and 2B and explained in more detail below.

Returning to FIG. 2A, communication thread 200 may include an identification header that identifies the patient being discussed/monitored via the communication thread. In the illustrated example, communication thread 200 is specific to patient ID 1234. In the illustrated portion of communication thread 200, communication is occurring between a care provider (Dr. Smith) and three virtual healthcare assistants, an EMR VHA, a predictive VHA, and a guideline VHA. Communication thread 200 is being viewed by Dr. Smith, although any authenticated/approved user may view communication thread 200. As shown by the first message from the top, Dr. Smith is requesting medical information relating to the patient from one of the VHAs by asking, in natural language, for a heart rate graph ("Could I get the HR graph please"). In response, the EMR VHA sends an image of the patient's heart rate graph, which may be obtained or assembled from the patient's EMR data. The image of the heart rate graph is viewable in the communication thread and may also be selected via suitable user input to view in a different form, such as via the patient dashboard.

At a later time (e.g., 4:00 PM), the predictive VHA outputs an alert/notification in the communication thread indicating a change in patient status, herein a deterioration in vitals. The alert is accompanied by a suggested course of action that a care provider may take, including checking respiratory rate and mental state. The predictive VHA issues another alert at 5:00 PM indicating that sepsis is suspected based on a quick SOFA score (qSOFA), owing to low systolic blood pressure and a low Glasgow coma scale. The alerts issued by the predictive VHA may include links to the patient dashboard, for example, allowing a user to select a link to launch the dashboard and view the medical data relating to the alerts. For example, the alert "systolic BP is less than 100 mmHg" is shown in underline, indicating a link to additional information is available. A user may select the link via a suitable input, such as via a mouse click, touch input, or voice command. As will be explained in more detail below, selecting a link with a first selection (e.g., a double click) may launch the patient dashboard (as shown in FIG. 3). Selecting a link with a second selection (e.g., a single click or a hover) may launch a preview where only the patient's blood pressure graph is shown (as explained in more detail below with respect to FIG. 6).

In response to the alert regarding the potential sepsis, Dr. Smith asks for guidelines at 5:01 PM. Because the predictive VHA had immediately previously issued the alert regarding the possible sepsis due to the qSOFA score, the guideline VHA may assume that the guidelines being requested by Dr. Smith include guidelines for sepsis based on a qSOFA score. In response, the guideline VHA retrieves guidelines from an external guideline service relating to qSOFA scores and outputs the guidelines into the communication thread. As shown, only a portion of the guidelines are displayed in the communication thread. By selecting the link (the underlined "qSofa guidelines"), the user may be taken to a different interface where the full guidelines are displayed, or the full guidelines may be displayed over the top of the still-displayed communication thread.

Communication thread 200 continues in FIG. 2B. Therein, after the guideline VHA obtains the guidelines for sepsis based on the qSOFA score, at 5:04 PM the lab VHA outputs a recommended diagnostic lab test for confirming that the patient has sepsis, herein a PCT test. The lab VHA may obtain the recommended diagnostic lab test from the guidelines obtained by the guideline VHA, or the lab VHA may determine from the conversation ongoing on the communication thread that sepsis is suggested and obtain the recommended diagnostic test. Additionally, at 5:06 PM, the lab VHA provides an estimated time of arrival of the results for a PCT test, which may be determined based on staff availability (for both the blood draw to acquire the specimen to be tested and for performing the PCT test), average PCT test timings, and instrument availability/queue. The care provider (Dr. Smith) subsequently orders the PCT test. The test may be ordered through traditional mechanisms (e.g., a care provider submitting a request directly to the laboratory); however, at least in some examples, the lab VHA, upon determining that the lab test has been ordered, may concurrently notify the lab (e.g., via sending a message to the lab service/LIS) of the ordered lab test. In some examples, the lab VHA may notify the lab of the recommend lab test in a proactive manner, before the care provider has ordered the lab test. For example, the lab VHA may notify the lab (through the lab service/LIS) that a PCT test has been recommended for patient, which may allow the lab to prepare accordingly (e.g., manage staffing, ordering reagents, etc.). The lab VHA may also notify the lab of the patient status and suggest a priority for the lab test sample.

Further, the care provider requests to receive status updates for the PCT test in the message sent at 5:08 PM. As a result, the lab VHA tracks the status of the lab test, from patient specimen collection, transport of the patient specimen to the lab, processing of the patient specimen, and final test results. At 5:15, the lab VHA outputs a notification that the patient specimen has arrived at the lab and provides an updated estimated time for the test results to be available. At 5:45, when the lab VHA determines that the PCT test results are available, the lab VHA outputs a notification on the communication thread 200 that the PCT test results are available, including a link to the test results (which may be stored as part of the patient EMR). By selecting the link (e.g., with a cursor 204), the dashboard for patient ID 1234 may be launched, as explained below. The dashboard may include the test results along with other relevant information Thus, the care provider may be notified in real time when the test results are available, which may reduce delays in diagnostic/treatment decision making and may reduce disruptive and/or time consuming inquiries by the care provider to the lab. In some examples, the test results may be displayed in the communication thread. For example, if the user hovers the cursor over the link, a preview of the lab test results may be displayed over or within the communication thread.

At 5:50, the care provider enters a treatment plan for the patient, including administering an antibiotic to address the potential that the sepsis could be caused by bacteria. The command to administer the antibiotic may be made by Dr. Smith to another care provider also treating the patient (e.g., by voice and picked up by the listening VHA or by Dr. Smith directly inputting the command into the communication thread), or Dr. Smith may be generally notifying the VHAs and/or other care providers of the treatment plan for record-keeping and information sharing purposes. In response to the notification from the care provider the antibiotic (e.g., antibiotic X) is going to be administered, the pharmacy VHA may be joined to the conversation occurring on the communication thread 200 (or the pharmacy VHA may be notified of the pending treatment from the listening VHA or from another mechanism, such as from an order being placed by the care provider to the pharmacy). When the pharmacy VHA learns of the pending antibiotic treatment, the pharmacy VHA may notify the pharmacy and confirm if the pharmacy has that particular medication, provide an estimated time until the medication is available for administration, etc. Thus, as shown, at 5:55, the pharmacy VHA outputs a notification in the communication thread that antibiotic X is in stock at the pharmacy and that the request for the antibiotic has been filled and the antibiotic is en route to the care provider for administration.

While not shown in FIGS. 2A and 2B, communication thread 200 may include a search box/functionality where a user may search for past messages on the communication thread. For example, a user may enter a command (by voice or text) requesting that all messages related to the patient's heart rate be displayed. Also displayed on display device 202 is a communication thread button 206 and a dashboard button 208. In FIGS. 2A and 2B, the user is viewing the communication thread 200 occurring on the communication channel. Hence, the communication thread button 206 is highlighted. To switch to the dashboard for patient ID 1234, the user may select the dashboard button 208.

FIG. 3 shows an example dashboard 300 that may be displayed on display device 202 or other suitable device. Dashboard 300 may be displayed in response to a user input to the communication thread 200, for example by selecting a link within medical information displayed in communication thread, as explained above, or in response to selection of the dashboard button 208. However, dashboard 300 may be displayed in response to other inputs, such as in response to a user input selecting the dashboard from the collaborative system interface of FIG. 10 that includes a global view of multiple communication threads and dashboards. Additionally, FIG. 3 shows a side bar 302 displayed along with dashboard 300 showing patient dashboards for the patients Dr. Smith is currently attending. User input to the side bar may launch a different dashboard, for example Dr. Smith may select to view each of the currently available dashboards to quickly assess the status of each patient.

Dashboard 300 may be configured to display patient medical information based on the current patient state and user-configured settings. For example, a dashboard for a patient that is being treated at the medical facility for pneumonia may be configured to display different medical information than a dashboard for a patient that is being treated at the medical facility for a stroke. In some examples, when a patient is admitted at the medical facility, a dashboard may be generated automatically for the patient based on the reason of admittance (e.g., pneumonia), thereby including the most relevant patient medical information for the patient's condition, such as blood oxygen level and respiration rate. A user may also configure which medical data to view via the dashboard, for example a doctor attending to the patient may choose to view heart rate rather than respiration rate.

The medical information that is displayed on the dashboard may be obtained from one or more monitoring devices currently monitoring the patient, such that the medical information is displayed on the dashboard in a real-time (or near real-time) manner. Additionally or alternatively, the medical information that is displayed on the dashboard may be obtained from the patient's EMR, the digital twin associated with the patient, and/or the communication thread. As explained above, one or more VHAs may obtain patient medical information from the patient's EMR, the monitoring devices, guideline services, or other sources and include the obtained medical information as a message in a communication thread on the communication channel. To view the medical information in greater detail, the user may select the medical information from the communication thread, where the medical information may then be displayed in the dashboard.

Additional information may also be displayed via the dashboard, such as patient information (location, demographics, medical history), care provider information (such as which doctors, nurses, and/or other care providers are attending to the patient), and a timeline of selected or relevant messages from the communication thread. For example, the most recent alerts may be displayed as a timeline on the dashboard.

Referring to dashboard 300 as an example, patient information 304 is displayed at the top of the dashboard, including patient identification and location. Care provider information 306 is also displayed in dashboard 300, including current care providers for the patient. Additionally, a user interface control button 308 is shown that, when selected, may allow the care provider viewing dashboard 300 to view and interact with the communication thread.

Dashboard 300 further includes real-time medical information indicators 310. As shown, the indicators 310 include a SOFA score and blood glucose level, depicted as gauge charts with respective needles that move to indicate current SOFA score and blood glucose relative to a range of possible SOFA scores and blood glucose levels. While not shown in FIG. 3, the gauge charts may include color coding for quick determination of normal, intermediate, and high scores/levels, for example. The gauge charts shown are exemplary in nature and patient medical information may be shown in other forms.

Dashboard further includes medical history trends, including a first graph 312 depicting mean arterial blood pressure trend (e.g., blood pressure as a function of time) and a second graph 314 depicting blood glucose trend (e.g., blood pressure as a function of time). The medical history trends shown in FIG. 3 may be displayed on the dashboard in response to a request from a user (e.g., in response to a care provider selecting a link to patient medical history from a communication thread), due to a preconfigured dashboard setting, or other suitable trigger. For example, as shown in FIG. 2A, the predictive VHA issued an alert at 5:00 PM that included reference to patient blood pressure in the form of a link. When the link is selected (e.g., via cursor 204), the dashboard 300 may be displayed showing the first graph 312 of the patient's blood pressure trend.

Dashboard 300 further includes a recent lab test results section 316, where the results from recent lab tests may be displayed. For example, the user may have selected the link to the available PCT test results displayed as part of the communication thread 200 of FIG. 2B, which may result in display of dashboard 300. Via the recent lab test results section 316, the user (care provider) may be notified that the PCT test for that patient is relatively high and thus sepsis is confirmed or suspected.

As explained earlier, one or more of the virtual healthcare assistants may be configured to monitor patient vital signs, via the output from the monitoring devices, the information stored in the digital twin, or other source. If a vital sign (or other health parameter) meets a predetermined condition, the one or more virtual healthcare assistants may be configured to output an alert to notify the one or more care providers attending the patient that patient follow-up may be needed. The alerts may be included in the communication thread, as discussed above. Additionally or alternatively, the alerts may be displayed on the dashboard. As shown, first graph 312 includes two alerts, each alert issued when mean arterial blood pressure dropped below a threshold, such as 80 mmHg, or trended in an unexpected way, such as five consecutively decreasing values which may or may not be below the 80 mmHg threshold. Selection of an alert may trigger display of a portion of the communication thread occurring on the communication channel where the alert was referenced.

Thus, as shown in FIG. 4, in response to user input selecting the second alert displayed on the dashboard 300 (e.g., the "alert 2" box) via cursor 204, a portion 402 of the communication thread 200 shown in FIG. 2A is displayed over dashboard 300. The portion 402 displayed may include only the portion of the communication thread that references the medical information that triggered the alert, and may also include additional messages around the message referencing the alert, in order to place the alert in context. In this way, a user may be able to quickly determine what else may have occurred around the time the alert was issued, determine if attending care providers administered treatment, or determine other relevant information. The portion 402 may not include the most recent messages in the communication thread, in some examples. Further, a user may not have access to the full communication thread when viewing the portion, and may not be able to interact (e.g., send messages) with the communication channel. Thus, a different selection on the dashboard may enable a user to view the full communication thread.

Additionally or alternatively, when viewing the portion of the communication thread, the user may scroll to view other portions of the communication thread or may enter another input to the portion of the communication thread to enable viewing of the full version of the communication thread. Alternatively, instead of showing a snippet from the communication channel, the full version of the communication thread may be displayed, with the focus point being the point in the communication channel that references the alert (which may enable the user to look before and after that point of the thread if desired). In another example, only the snippet of the communication thread may be displayed and if the snippet is selected, the full version of the communication thread may be displayed. In this way, either automatically or upon a further user input, the use may be able to interact with the communication thread (e.g., send a message via the communication thread).

Thus, the collaborative healthcare system shown in FIG. 1 may generate communication channel-dashboard pairs for each patient associated with the collaborative healthcare system. The collaborative healthcare system may include one or more computing devices, such as the care provider device 134. The computing device may include a display screen, and the computing device may be configured to display on the screen a dashboard. The dashboard may include patient medical information, such as diagnostic lab test information (e.g., lab test results, pending lab tests that have been ordered but not yet fulfilled, status updates for pending lab tests, and so forth). The computing device may additionally be configured to display on the screen an alert related to the patient medical information. For example, as shown in FIG. 3, dashboard 300 may be displayed on a screen of a computing device (e.g., display device 202, which may be a screen of a computing device such as care provider device 134). Dashboard 300 may display patient medical information, such as the graph of the blood pressure trend of the patient (e.g., first graph 312) and recent lab results. The displayed medical information may include an alert, such as alert 2 shown on first graph 312.

The alert may be selectable to launch a communication thread between a care provider and a virtual healthcare assistant. For example, as shown in FIG. 4, selection of alert 2 launches a communication thread between a care provider (Dr. Smith) and a virtual healthcare assistant (the predictive VHA). The selection of the alert enables a portion of the communication thread that references the displayed patient medical information to be seen within the communication thread. For example, FIG. 4 shows that in response to selection of alert 2, a portion 402 of the communication thread 202 (shown in FIG. 2A) is displayed. The portion 402 includes reference to patient blood pressure, which is also displayed on the patient dashboard. Further, the alert may be displayed on the dashboard (at least initially) while the communication thread is in an un-launched state. For example, the alert may be displayed on dashboard 300 without display of the communication thread, e.g., while the communication thread is un-launched. In some examples, the full communication thread may be displayed rather than just a portion, with the full communication thread focused at the portion that references the patient blood pressure. According to some embodiments, the communication thread and the dashboard may both be displayed simultaneously on the display device.

In some examples, such as when patient state changes or when a pending lab test is delayed or cancelled, an alert related to diagnostic lab test information may be displayed on the dashboard. For example, FIG. 12 shows an example dashboard 1200. Dashboard 1200 may be similar to dashboard 300, but may be reflective of patient information available at a time earlier than when dashboard 300 was displayed. For example, dashboard 1200 may be displayed in response to a care provider request made before the PCT test results were available, but after the PCT test had been ordered. Dashboard 1200 includes a pending lab tests section 1202, where lab tests awaiting results are shown. An alert is associated with the PCT test, in the form of an exclamation point. If a user were to select the alert, the portion of the communication thread 200 where status update for the PCT test was provided (e.g., a portion including the message sent by the lab VHA at 5:15) may be displayed, so that the care provider may view the updated ETA for the lab test. Similar alerts may be displayed if patient state changes and thus the priority ranking for the pending lab test changes, the pending lab test is delayed or cancelled by the lab, etc.

In this way, the computing device provides a specific manner of displaying a limited set of information (e.g., the portion of the communication thread that specifically references medical information displayed on the dashboard) to the user, rather than using conventional user interface methods to display a generic index/list on a computer that may require the user to step through multiple menus and/or lists of communications and alerts to find the relevant portion of communication regarding the medical information. The dashboard interface-communication thread link disclosed herein may be advantageous because it avoids a user having to scroll around and switch views multiple times to find desired data/functionality, thereby preventing drilling down through many layers to get the desired data/functionality which may be slow, complex, and difficult to learn. The disclosed dashboard interface-communication thread link may improve the efficiency of using the computing device by bringing together the portion of the communication thread most relevant to the user (as it relates to the displayed medical information) and the dashboard actually displaying the medical information, allowing the user to view the most relevant information on the communication thread without actually opening up the communication thread. The speed of a user's navigation through various views and windows may be improved because the disclosed link between the dashboard and the communication thread saves the user from navigating to the communication thread from the dashboard, opening the communication thread up, and then navigating within the communication thread to enable the portion of interest to be seen or a function of interest to be activated.

FIG. 5 shows a full version 502 of the communication thread that may be displayed in response to user input at the control button 308 (shown by cursor 204). The full version 502 may include the most recent messages sent on the communication channel. For example, full version 502 includes messages not shown in the portion 402 of the communication thread. Further, a user interface user input block is present at the bottom of the communication thread, via which a user may type a message to be sent on the communication channel. Due to space constraints, not all messages on the full version of the communication thread may be visible at one time, and thus the full version 502 may include a prompt where the user may swipe or enter other input to view additional messages. Additionally, while FIG. 5 shows the full version 502 superimposed over the dashboard 300, it is to be understood that in other examples, the dashboard may be replaced by the communication thread on the display device.

FIG. 6 shows an example where the full version 502 of the communication thread is displayed on display device 202 as a separate interface, without the dashboard also being displayed. In the example shown in FIG. 6, a user input to a link on the communication thread ("test results available here") may trigger display of a preview 600 of the lab test results. As shown, preview 600 may include the PCT test results showing the relatively high PCT level for the patient. The preview 600 may be displayed in response to a single click or mouse hover over the link, for example.

Thus, the collaborative healthcare system shown in FIG. 1 may generate communication thread-dashboard pairs for each patient associated with the collaborative healthcare system. The collaborative healthcare system may include one or more computing devices, such as the care provider device 134. The computing device may include a display screen, and the computing device may be configured to display on the screen a communication thread. The computing device may additionally be configured to display on the screen a dashboard that can be reached directly from the communication thread. For example, as shown in FIGS. 2A and 2B, the communication thread may include a link that when selected launches a dashboard, such as the dashboard 300 shown in FIG. 3.

The communication thread displays communication between a care provider and a virtual healthcare assistant, and the communication thread includes medical information of a patient. At least a portion of the displayed medical information is selectable to launch the dashboard and enable the selected medical information to be seen within the dashboard. For example, referring to FIG. 2B, the communication thread includes a link referencing patient medical information (herein, lab test results), and selection of the link launches some or all of the dashboard. The dashboard includes display of the patient medical information included in the link (e.g., the lab test results). In an example, selection of the link may launch a full version of the dashboard, as shown in FIG. 3. In another example, selection of the link may launch only a portion of the dashboard, such as the preview shown in FIG. 6. The communication thread may be displayed while the dashboard is in an un-launched state, at least initially. For example, FIGS. 2A and 2B show the communication thread being displayed without display of the dashboard, and thus the dashboard may be unlaunched until the link the communication thread is selected.

In this way, the computing device provides a specific manner of displaying a limited set of information (e.g., the dashboard that specifically includes medical information referenced in the communication thread) to the user, rather than using conventional user interface methods to display a generic index/list on a computer that may require the user to step through multiple menus and/or lists of communications and alerts to find the relevant medical information. The communication thread-dashboard interface link disclosed herein may be advantageous because it avoids a user having to scroll around and switch views multiple times to find desired data/functionality, thereby preventing drilling down through many layers to get the desired data/functionality which may be slow, complex, and difficult to learn. The disclosed communication thread-dashboard interface link may improve the efficiency of using the computing device by bringing together the medical information most relevant to the user (via the dashboard) and the communication thread referencing the medical information, allowing the user to view the most relevant medical information discussed on the communication thread without actually accessing an electronic medical record or separate interface where patient monitoring data may be displayed. The speed of a user's navigation through various views and windows may be improved because the disclosed link between the communication thread and dashboard saves the user from navigating to an electronic medical record database, opening the database up, and then navigating within the database to enable the medical information of interest to be seen or a function of interest to be activated.

Figure 11:
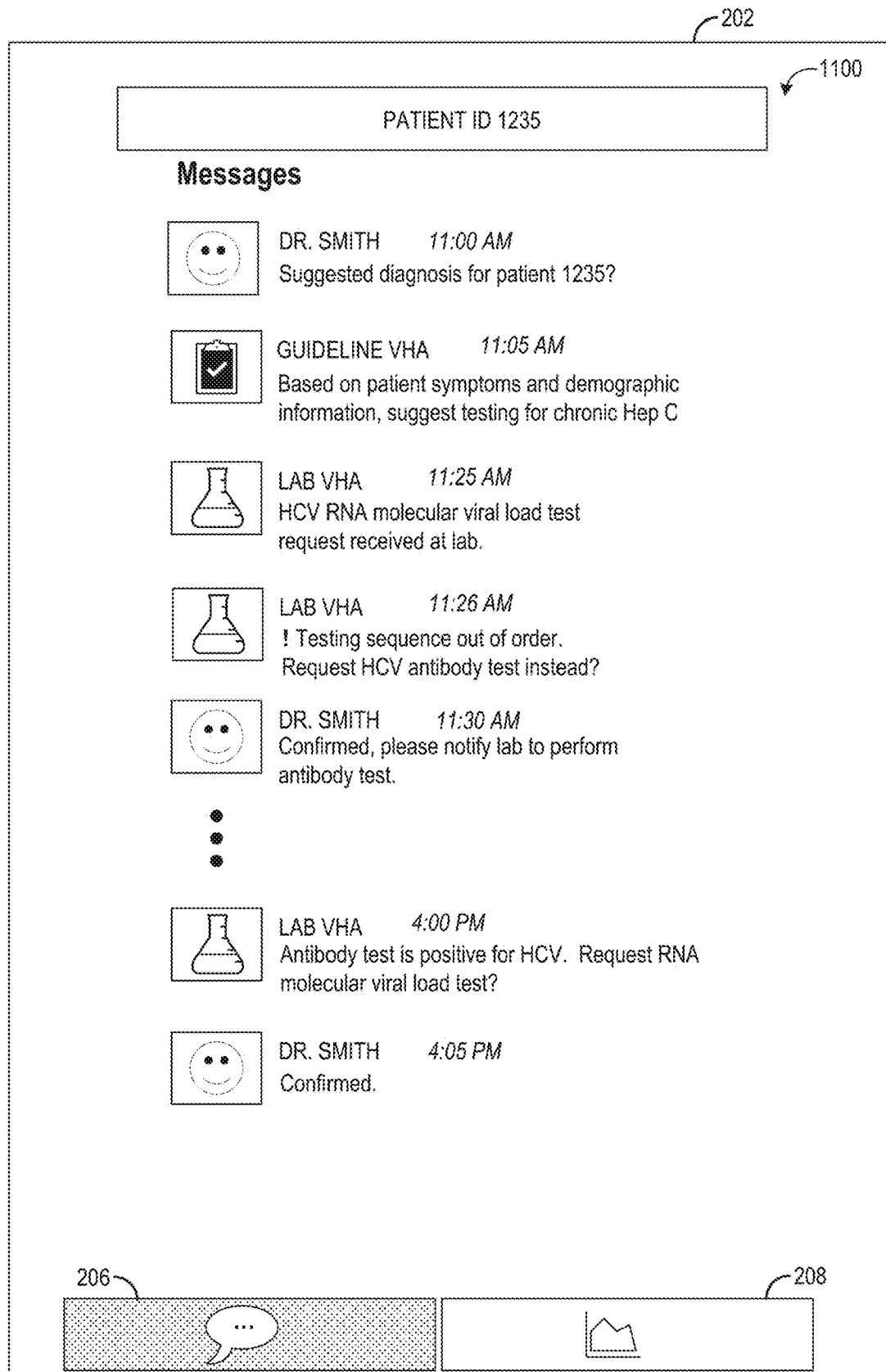
FIG. 11 shows an example display device displaying another communication thread occurring on a communication channel of the collaborative healthcare system.
Figure 12:
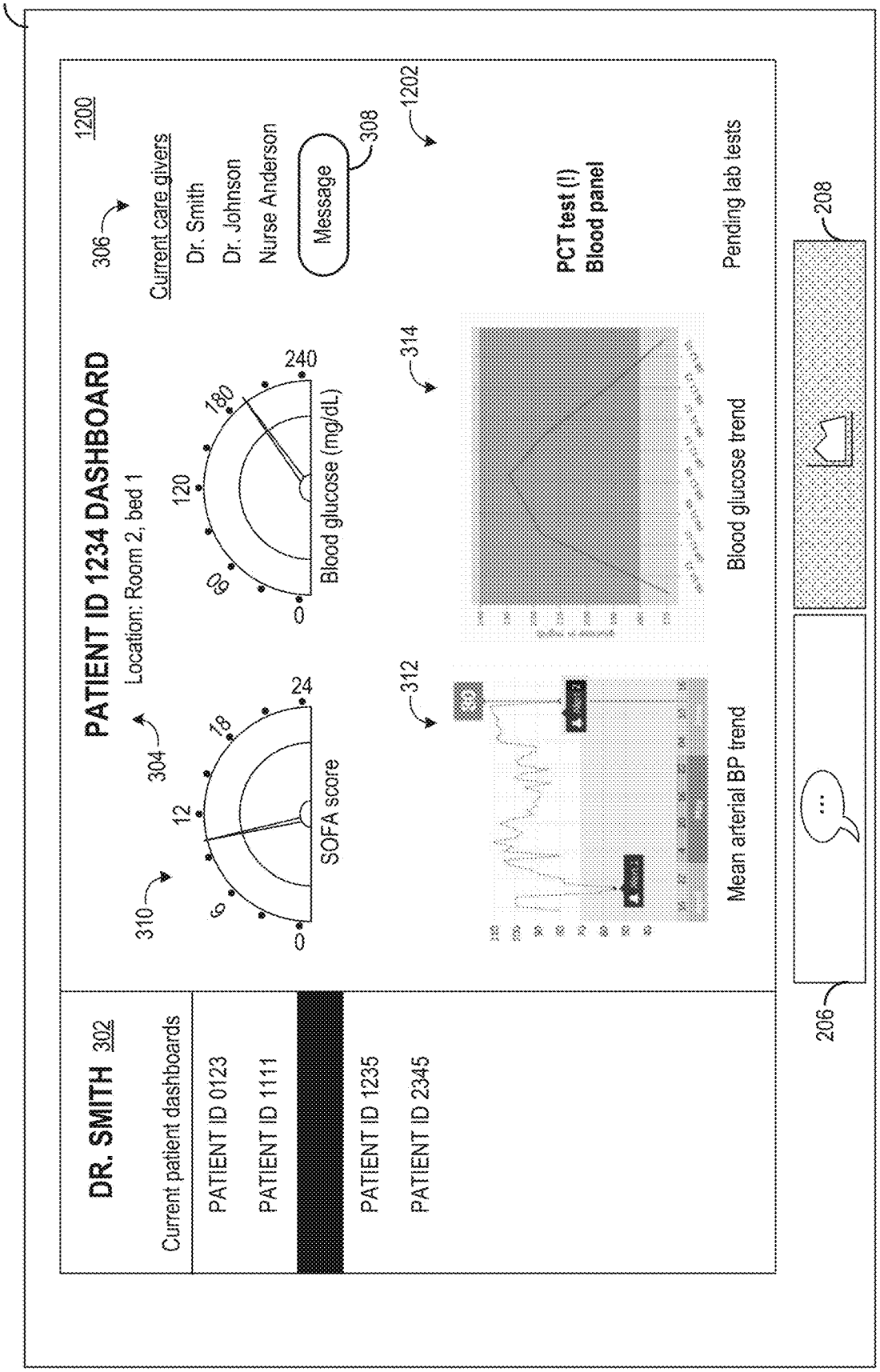
FIG. 12 shows a display device displaying a further instance of a dashboard of the collaborative healthcare system.

FIG. 11 shows a communication thread 1100 of a patient-specific communication channel, and as such may be a non-limiting example of communication thread 104. Communication thread 1100 may be displayed on the display device 202. Communication thread 1100 may be displayed in response to a user request to display the communication thread and may include an identification header that identifies the patient being discussed/monitored via the communication thread. In the illustrated example, communication thread 1100 is specific to patient ID 1235. In the illustrated portion of communication thread 1100, communication is occurring between a care provider (Dr. Smith) and two virtual healthcare assistants, a guideline VHA and a lab VHA. Communication thread 1100 is being viewed by Dr. Smith, although any authenticated/approved user may view communication thread 1100.

As shown by the first message from the top, Dr. Smith enters a request for a suggested diagnosis for the patient as a message on the communication thread. For example, the patient may be showing signs of deterioration, but the care providers may be uncertain of an exact cause of the deterioration. Thus, the VHAs (e.g., the guideline VHA) may be requested to provide suggestions for what may be causing the patient to deteriorate. In response, via a message sent at 11:05, the guideline VHA suggests testing the patient for chronic hepatitis C infection. The guideline VHA may determine that hepatitis C infection is a likely diagnosis based on the patient symptoms (heart rate, respiration rate, etc.) as determined by the data output by the monitoring devices and/or based on the digital twin of the patient as well as demographic information (e.g., patient age, geographic location). Dr. Smith or another care provider then submits an order to test the patient for hepatitis C.

The lab VHA identifies that a request for a hepatitis C virus (HCV) RNA molecular viral load test is received at the lab, based on communication with the lab system, for example, and outputs a notification to the communication thread at 11:25 the HCV RNA molecular viral load test order has been received at the lab. However, the lab VHA determines that, based on medical facility guidelines, an HCV antibody test should be conducted before RNA molecular viral load test. Thus, at 11:26, the lab VHA outputs a message to the communication thread alerting the care providers that the testing sequence is out of order, and asks the care providers if an HCV antibody test should be conducted instead. At 11:30, Dr. Smith sends a message confirming that the HCV antibody test should be performed. The lab VHA may then notify the lab system to test the patient specimen for HCV antibody.

In due course, the HCV antibody test results are ready, and the lab VHA notifies the care providers, via the communication thread, that the antibody test is positive for HCV. The lab VHA then asks if the care providers want to perform the recommended next test, which is the RNA molecular viral load test. Dr. Smith confirms via a message sent to the communication thread, and thus the lab VHA may notify the lab system that the RNA molecular viral load test is to be performed.

FIG. 7 is a flow chart illustrating a method 700 for a collaborative healthcare system serving a medical facility, such as a hospital. Method 700 may be executed by a processor of a computing device (such as processor(s) 132 of server system 102 of FIG. 1) according to instructions stored on a non-transitory memory of the device (e.g., memory 130 shown in FIG. 1) in combination with the various signals received at the server system from components of the collaborative healthcare system (e.g., patient medical data signals from monitoring devices 120, communication from hospital operational systems 118, etc.) and signals sent from the server system to the care provider devices and/or other system components.

At 702, method 700 includes receiving a notification that a patient has been admitted to the medical facility. The notification may be received from the hospital operational systems, and may include a patient identifier, patient state (e.g., the condition for which the patient is being admitted), and care provider information. The care provider information may include identifiers of various care providers (such as doctors and nurses) that are currently attending to the patient.

At 704, method 700 includes generating a communication channel including a communication thread and a dashboard for the patient. In order to generate the communication channel, verified care providers of the patient (e.g., as indicated by the notification from the hospital operational systems) and one or more virtual healthcare assistants (VHAs) may be joined to the communication channel, as indicated at 706. The communication channel may facilitate text and/or rich-media based messages to be sent among all the verified care providers and VHAs that are joined to the communication channel. The one or more VHAs may include an EMR VHA, a guideline VHA, a predictive VHA, a listening VHA, a monitoring VHA, a lab VHA, a pharmacy VHA, and/or other VHAs. To join the channel, each VHA may receive a message that a new channel has been opened and the access application (e.g., executing on the server system 102) may add the VHAs to the eligible participants of the channel. Moreover, in some examples, not all available VHAs may be invited to all channels (e.g., a sepsis VHA may not be invited in a non-relevant case or the listening VHA may not be invited due to patient refusal to be monitored by recording).

Generating the dashboard may include configuring the dashboard based on the patient state and/or user settings, as indicated at 708. As explained previously, a patient dashboard may be a graphical user interface that facilitates display of patient medical information, such as real-time vital signs, medical history, treatment plan, and/or other information. The dashboard may also include relevant/desired messages from the communication thread. Which medical information to display on the dashboard and in what format may be determined based on the patient state (e.g., current medical condition for which the patient is being treated) and/or on user settings, which may be configured by the end-viewer of the dashboard. In this manner, different patients may have different medical information displayed on different dashboards, and different care providers may view different medical information for the same patient, if desired.

At 710, method 700 includes receiving text- and/or rich-media-based messages from the participants on the communication channel, including care providers and VHAs. During the course of patient care, care providers may communicate with each other on the communication channel via messages of the communication thread to coordinate care, give care instructions, and/or confirm appropriate care is being carried out. Further, care providers may send requests to the VHAs via the communication thread for various information related to the patient care, including patient medical history, care guidelines, predicted future patient state, recommended lab tests, etc. Further still, VHAs may send notifications via the communication thread of changes in patient state, patient medical history, patient care guidelines, predicted future patient states, lab test status, etc. The messages sent from a care provider may be sent from a care provider device (e.g., device 134) and received at the server system via a suitable connection (e.g., wired or wireless, such as via the Internet). The messages sent from the VHAs may be generated by the VHAs, which may be stored and executed on the server system, the cloud, and/or a remote device. As used herein, messages may refer to any suitable information sent and received on the communication thread, including but not limited to text messages (entered via typing, touch, or stylus input, voice input, or automatically generated by a VHA), images, voice messages (e.g., recordings of voice input), and videos.

At 712, method 700 includes distributing the received messages to other participants on the communication channel and saving the received messages as a communication thread. Each message that is sent to the server system may be tagged with various identifiers that identify the sender as well as the patient communication thread to which the message pertains (e.g., the patient identifier). The server system may then send the message to other participants of the communication channel, e.g., the care providers and/or VHAs that did not send the original message, and save the message as part of a saved communication thread. The saved communication thread may then be viewed by other users at other times, retrieved in response to a user request to view some or all of the communication thread, etc. However, in some examples, the device from which the original message was sent (e.g., the care provider device) may send the message to all other participants on the communication channel, and thus the server system may not distribute the message to the other participants.

At 714, method 700 includes receiving patient medical information. The patient medical information may be received from one or more patient monitoring devices that are configured to measure patient state and condition, including sensors that measure vital signs (e.g., blood pressure, heart rate, and blood oxygen level), diagnostic imaging modalities, microphones in proximity to the patient, and so forth. Additionally, the patient medical information may be received from the communication thread. For example, two care providers may be messaging each other on the communication thread and exchanging information relating to the patient, such as visual information (e.g., skin pallor, redness, or yellowness) of the patient that may indicative of patient state. One or more of the VHAs may be configured to parse the message and determine that relevant medical information is being exchanged and then save the medical information as messages within the communication thread.

At 716, method 700 includes updating a digital twin of the patient with the medical information. The digital twin may be a digital replica/representation of the patient that is saved at the computing device (e.g., digital twin 108 saved on the server system 102). The digital twin may include patient demographic information, medical history, and other information to provide, to the extent possible, a simulation/representation of the current patient medical state. When new or updated medical information is received, the digital twin may be updated to reflect the most recent patient medical state. The digital twin may be accessed (e.g., by one or more of the VHAs) to retrieve patient medical information, predict future patient states (e.g., simulations may be performed using the information stored in the digital twin to determine the probability of the patient developing a certain condition), identify the most relevant lab tests to be conducted to diagnose a patient condition, and provide appropriate context when retrieving care guidelines.

At 718, method 700 includes outputting the communication thread for display when prompted. In an example, the prompt may include an explicit request to view the communication thread for the patient, entered by selection of an appropriate link/control button on the patient dashboard or selection of the patient's communication thread from a collaborative interface, as indicated at 720. For example, as shown in FIG. 5, a message button may be displayed via the patient dashboard, and selection of the message button may trigger display of the communication thread for that patient. In another example, as shown in FIG. 10, a patient link may be selected to launch the communication thread from a collaborative system interface. In an example, the communication thread may be output for display automatically in response to a request from one or more of the VHAs, as indicated at 722. For example, a listening VHA may detect that one or more care providers are discussing a particular piece of the patient's medical history, and the listening VHA may send a portion of the communication thread that includes reference to the particular piece of medical history to the care provider's device for display. In another example, a VHA may detect that a patient vital sign has reached a level that may indicate a potential urgent patient condition and the VHA may output an alert regarding the vital sign on the communication channel. In some examples, issue of such an alert may prompt automatic display of the communication thread on each participant's display device.

At 724, method 700 includes outputting the dashboard for display when prompted. In an example, the prompt may include an explicit request to view the dashboard for the patient, entered by selection of an appropriate link/control button on the communication thread or selection of the patient's dashboard from a collaborative interface, as indicated at 726. For example, as shown in FIGS. 2A and 2B, a link to the dashboard may be displayed in the communication thread, and selecting the link may trigger display of the dashboard for that patient. In an example, the dashboard may be output for display automatically in response to a request from one or more of the VHAs, as indicated at 728. For example, the listening VHA may detect that a care provider is discussing the patient's current medical state and may automatically output the dashboard for display on the care provider's device so that the care provider may view patient medical information displayed in the dashboard that relates to the current medical state being discussed. Method 700 then returns.

FIG. 8 is a flow chart illustrating a method 800 for sending medical information to a care provider via one or more virtual healthcare assistants. Method 800 may be executed by a processor of a computing device (such as processor(s) 132 of server system 102 of FIG. 1) according to instructions stored on a non-transitory memory of the device (e.g., memory 130 shown in FIG. 1). As explained above with respect to FIG. 1, the server system 102 may store/execute one or more virtual healthcare assistants (VHAs) that are configured to perform certain tasks related to providing medical information of the patient to the one or more care providers attending to the patient, as explained below.

At 802, method 800 includes receiving a request to provide information to one or more care providers. The request may be provided via a message from a care provider that includes a request for medical information relating to a patient, as indicated at 804. For example, as explained previously, each patient may have a dedicated communication channel including a communication thread that facilitates communication among the care providers treating the patient and one or more VHAs. When a care provider sends a message on the communication thread, the message may be received at the server system and the message may be analyzed to determine which patient the care provider is referring to and what information is being requested. The information request may be an explicit request, where the care provider explicitly asks for certain medical information, such as "please send me the patient's heart rate over the last four hours." In other examples, the request may be implicit. Implicit requests may include assumptions (on the part of the VHAs executing on the server system) that certain medical information may be helpful, such as when a change in patient vital signs is detected, that are not accompanied by an actual request by the care provider.

In some examples, the request to provide information to the care provider may be provided via the lab system (e.g., lab system 125) or according to scheduled notifications, as indicated at 806. For example, when a lab test for a patient is pending, the lab system may send updates of the status of the lab test (e.g., in queue, being processed, results available). In other examples, a care provider may have set scheduled notifications of the pending lab test, such as requesting to be notified of an estimated time until the test results are available, to be notified when the status of the lab test changes, and/or to be notified when the results of the lab test are available.

At 808, method 800 includes determining the appropriate VHA for handing the request for the medical information. For example, if the request includes a request for patient medical history, the EMR VHA may handle the request. If the request includes a request for patient care guidelines, the guideline VHA may handle the request. If the request includes a request for lab test information, the request may be handled by the lab VHA. In some examples, each VHA may process a received message to understand (in natural language) the intent of the message and determine if the intent of the message includes a task that the VHA is trained/configured to perform. In some examples, the server system may include a central entity configured to understand the intent of the message (e.g., from the natural language of the message) and determine which VHA is best configured to handle the request. Then, the mapping from intent (and VHAs) to a specific API of a specific VHA is one-to-one, that is, only one VHA handles a specific intent (or intent-entity combination).

At 810, method 800 includes retrieving, with the selected VHA, the requested information. The requested information may be retrieved from the patient's EMR, as indicated at 812, or from the digital twin of the patient. In other examples, the requested information may be retrieved from a guideline service or predictive service, as indicated at 814. In still further examples, the requested information may be retrieved from the one or more monitoring devices that are currently monitoring the patient. In still further examples, as indicated at 815, the requested information may be retrieved from a lab (e.g., the lab system) or pharmacy (e.g., pharmacy system 127). At 816, method 800 includes sending a message including the retrieved medical information to the care provider via the communication channel. In an example, sending the message includes sending a message including information that includes an estimated time of arrival (ETA) for one or more pending lab tests, as indicated at 818. For example, when a care provider orders a lab test, the lab VHA (and in coordination with the lab system, at least in some examples) may obtain an ETA for when the results of that lab test will be available, and the lab VHA may send a message including the ETA. The ETA may be determined at various points while the lab test is pending (e.g., when the test is ordered, when the specimen is received at the lab, when the specimen is being processed). Further, in some examples, the ETA may be determined before the test is ordered, so that the care provider may determine if another test would be preferred if the wait time is undesirably long. As explained previously, the ETA for the lab test may be determined according to lab-wide historical data (e.g., average wait times for that particular type of lab test), the number of patient specimens in the current queue, any equipment issues or reagent or staffing shortages, and so forth.

In some examples, sending the message includes sending a message where the information in the message includes a notification of any duplicate, missing, or mistakenly ordered lab tests, as indicated at 820. For example, if a care provider orders a lab test for a patient, or if the lab VHA predicts that a care provider may order a lab test for a patient (based on a predicted diagnosis, a monitored care provider conversation, current patient symptoms, and the like), the lab VHA may determine whether that lab test was recently ordered (e.g., within the prior 24 or 48 hours) by accessing information from the patient EMR, digital twin, and/or the lab system. If the lab test was performed recently, the lab VHA may output a notification to notify the care provider that the lab test was recently performed (or is currently in process). If guidelines are available that dictate which lab tests should be conducted for a patient (based on current patient symptoms, predicted patient state, and/or care provider provided diagnosis of patient state), and if any of those lab tests have not been ordered (or if the guidelines dictate an order in which the lab tests should be conducted, and the lab tests have not been requested in the proper order), the lab VHA may output a notification to suggest to the care provider that a particular lab test or lab test sequence should be ordered.

In a still further example, sending the message includes sending a message where the information in the message includes a notification of delayed or cancelled lab tests, as indicated at 822. Once a lab test has been ordered, equipment, staffing, reagent, or specimen issues may cause an unanticipated delay in receiving the test results. The lab VHA may track the status of an ordered lab test, and may receive indications (e.g., via the lab system) if the equipment used to analyze the patient specimen for the lab test is having issues (e.g., due to mechanical degradation, control errors, or other issues), if the lab is understaffed, if reagents used in the lab test are out of stock, or if the patient specimen is lost, corrupted, or otherwise unusable in the lab test. If the lab results are delayed or cancelled to equipment issues, reagent shortages, or understaffing, the lab VHA may output a message indicating the anticipated length of the delay and the reason for the delay, which may allow the care provider to determine if a different test should be conducted, if the test should be sent to a different (e.g., off-site) lab, if a new patient specimen should be obtained, and so forth. Method 800 then returns.

Figure 9:
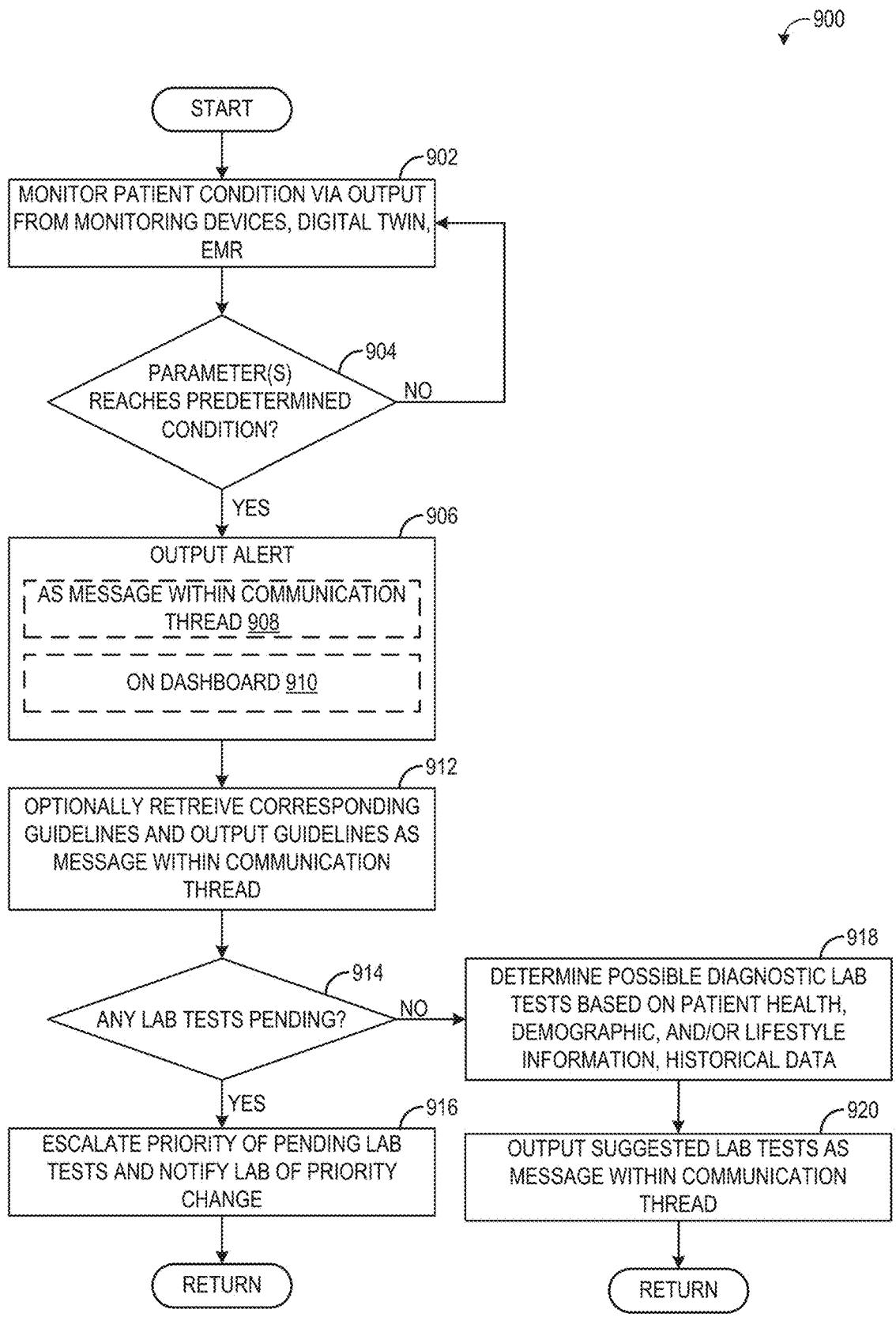

FIG. 9 is a flow chart illustrating a method 900 for monitoring a patient state via one or more virtual healthcare assistants. Method 900 may be executed by a processor of a computing device (such as processor(s) 132 of server system 102 of FIG. 1) according to instructions stored on a non-transitory memory of the device (e.g., memory 130 shown in FIG. 1). As explained above with respect to FIG. 1, the server system 102 may store/execute one or more virtual healthcare assistants (VHAs) that are configured to perform certain tasks related to monitoring a state or condition of the patient and notifying the care providers of the patient state, should the state change, as explained below.

At 902, method 900 includes monitoring the patient condition via output from one or more monitoring devices monitoring the patient (e.g., monitoring devices 120), a digital twin of the patient (e.g., digital twin 108), and/or an electronic medical record of the patient. As explained previously, one or more of the VHAs, such as the monitoring VHA, predictive VHA, and/or guideline VHA, may receive medical data regarding the patient's state in order to determine if the patient condition has changed, predict future patient events, etc. At 904, method 900 includes determining if one or more parameters of the patient condition has reached a predetermined condition. The one or more parameters may include vital signs or other health parameters that are currently being monitored, and the one or more parameters reaching the predetermined condition may include the one or more parameters reaching an abnormal condition, e.g., a condition that may indicate potential urgent patient conditions that necessitate treatment or evaluation from a care provider. For example, a parameter may include heart rate, and the heart rate reaching a predetermined condition may include the heart rate reaching a threshold, such as the heart rate dropping below a threshold heart rate. The abnormal condition (e.g., the threshold heart rate) may be based on a baseline condition for that patient. In the example of the heart rate, the patient may have a baseline heart rate of 75 bpm, which may represent an average of a plurality of heart rates of the patient measured over time while the patient is at rest. The threshold heart rate may be based on the baseline heart rate, such as equal to the baseline heart rate or a degree lower than the baseline heart rate (e.g., 75% of the baseline).

Other parameters that may be monitored include respiration rate, blood oxygen saturation, blood glucose, patient mental state, and so forth. Reaching the condition may include reaching a condition relative to a threshold, such as dropping below the threshold (as explained above with respect to the heart rate), exceeding the threshold (for example, a glucose level that exceeds a threshold may be indicative of an urgent condition), or other condition relative to a threshold, or an unusual trend, such as three consecutively decreasing values, but may still be above the lower threshold. In still further examples, rather than monitor the value of a given parameter relative to a fixed threshold, method 900 may include detecting if a parameter has changed (e.g., by a threshold amount such as increased or decreased by 10% or more). Further, method 900 may include detecting if a set of parameters has changed in a specific manner, or may include determining if one or more parameters are indicative of a potential health issue. For example, the predictive VHA may be configured to enter a set of parameters (e.g., obtained by the monitoring VHA) into an external prediction service to determine if the parameters are indicative of a yet-undiagnosed or untreated medical condition. Alternative examples may include changes in multiple parameters when in combination may indicate a deteriorating patient condition, even if no individual threshold is breached.

If none of the parameters reaches a predetermined (e.g., abnormal) condition, method 900 returns to 902 and continues to monitor the patient condition. If one or more of the parameters does reach a predetermined condition, method 900 proceeds to 906 to output an alert referencing the one or more parameters. The alert may be output as a message within the communication thread on the communication channel for that patient, as indicated at 908. For example, as shown in FIG. 2A, one of the VHAs (the predictive VHA) sent an alert on the communication thread for Patient ID 1234 at 4:00 PM indicating a deterioration in vitals was detected; another set of alerts was sent at 5:00 PM from the predictive VHA indicating suspected sepsis due to low blood pressure and a low Glasgow coma scale score. Additionally or alternatively, the alert may be output on the dashboard for the patient, as indicated at 910. For example, as shown in FIG. 3, two alerts are displayed on the blood pressure trend graph displayed within dashboard 300.

In some examples, in order to trigger an alert, only one parameter may need to reach its condition relative to its threshold. For example, a large drop in heart rate may trigger an alert regardless of the state of other parameters. In other examples, two or more parameters may need to reach respective conditions relative to respective thresholds to trigger an alert. For example, a small drop in heart rate coupled with a drop in blood oxygen saturation may trigger an alert, while only the small drop in heart rate alone may not trigger an alert. As such, a given parameter (e.g., heart rate) may actually be associated with multiple thresholds, such that dropping below a first threshold (e.g., 75% of the baseline heart rate) may trigger an alert while dropping below a second threshold (e.g., 90% of baseline heart rate) and not the first threshold may not trigger an alert unless the drop below the second threshold is also accompanied by a particular change in another parameter (e.g., a decrease in the blood oxygen level).

At 912, method 900 optionally includes retrieving corresponding guidelines and outputting the guidelines as a message within the communication thread on the communication channel. For example, if the change in parameters detected at 904 indicates a possibility of sepsis (as determined by the predictive VHA, for example), guidelines for treating sepsis may be output along with the alert indicating the possibility of sepsis.

At 914, method 900 includes determining if any lab tests for the monitored patient are currently pending. The lab VHA, for example, may be in communication with the lab system and/or may track all ongoing lab tests at the medical facility. If the lab VHA determines that one or more lab tests are currently pending for the monitored patient (where pending lab tests include lab tests that have been ordered but results not yet received), method 900 proceeds to 916 to escalate the priority of the pending lab test(s) and notify the lab (e.g., via the lab system) of the priority change. For example, the pending lab test may be in a queue at the lab, where the patient specimen may be in storage until all other specimens ahead of the patient specimen have been tested. Because the one or more patient parameters have changed/reached levels necessitating the alerts, patient health may be deteriorating and knowing the results of the lab tests may take on greater urgency. As such, the priority ranking of the specimen of the monitored patient (which may dictate the position of that specimen in the queue) may be adjusted so that the patient's lab test(s) is completed faster than would occur if the patient's state had remained stable.

Returning to 914, if no lab tests are currently pending for the patient, method 900 proceeds to 918 to determine one or more possible diagnostic lab tests based on patient health, demographic, and/or lifestyle information, along with historical data. As explained above with respect to FIG. 1, the lab VHA may include a testing model that may be executed when the current patient condition has not been diagnosed, or that may be executed when patient symptoms change. The testing model may output potential lab tests that may be performed to diagnose the patient, using current patient parameters as inputs (e.g., monitored health signs such as heart rate, demographic information such as patient age, geographic location, occupation, etc., lifestyle information such as travel history, exercise habits, etc., past and current diagnosed medical conditions, and the like) to the model. The testing model may be trained using the historical data and known outcomes for a plurality of past patients. The historical data may include parameters for the plurality of past patients (e.g., the parameters including monitored health signs, demographic information, lifestyle information, past and current diagnosed medical conditions, and the like). The known outcomes may include lab tests that were performed on those patients, and whether the lab tests were successful at diagnosing the patients. At 920, the suggested lab tests that are output by the testing model may be output as a message into the communication thread for the patient. Method 900 then returns.

While method 900 is illustrated herein as only escalating the priority of pending lab tests once the method determines that the patient has pending lab tests, it is to be understood that additional possible lab tests may be determined and suggested to care providers any time patient conditions change (or change to levels indicative of potential concern), regardless of whether the patient has any pending lab tests. Further, the possible lab tests may be determined automatically in response to monitored patient parameters, as described above, and the possible lab tests may be determined any time a care provider requests that possible lab tests be suggested.

The technical effect of generating communication channels including communication thread-dashboard pairs for each patient is to facilitate communication among care providers of the patient and allow virtual healthcare assistants to provide information retrieval and patient monitoring duties, thereby reducing care provider work load, increasing communication among care providers to avoid redundant or missed care of the patient, and allowing the communication occurring on the channel to be saved in a central location accessible by the care providers. By saving the communication on the channel, patient medical state, care decisions, and more may be viewable at a later time in context. The saved communication on the communication channel may be used to auto-populate medical records, reports, or other forms, and may be available for larger-scale (e.g., hospital-wide) analytics on treatment guidelines and patient outcomes.

An example provides for a method including generating a patient-specific collaboration channel comprising a patient-specific dashboard and a communication thread between a care provider team monitoring a patient and a virtual healthcare assistant; storing, at the channel, text- and/or rich media-based messages on the communication thread between one or more care providers of the care provider team and the virtual healthcare assistant, at least a portion of the messages on the communication thread including patient-specific medical data; and responsive to a prompt, outputting at least a portion of the communication thread that includes the patient-specific medical data to a display device. In a first example of the method, the patient-specific medical data comprises one or more possible diagnostic lab tests suggested by the virtual healthcare assistant to diagnose a condition of the patient, the virtual healthcare assistant utilizing a machine learning testing model to suggest the one or more possible diagnostic lab tests. In a second example of the method, which optionally includes the first example, the one or more possible diagnostic lab tests are suggested by the virtual healthcare assistant based on current monitored patient parameters, patient medical history, patient demographic information, and/or patient lifestyle information, and further based on historical information for a plurality of prior patients. In a third example of the method, which optionally includes one or both of the first and second examples, the historical information for the plurality of prior patients comprises, for each prior patient, monitored patient parameters, patient medical history, patient demographic information, and/or patient lifestyle information, and further includes known patient outcomes for each prior patient. In a fourth example of the method, which optionally includes one or more or each of the first through third examples, the prompt comprises an automatic prompt generated in response to one or more monitored patient parameters reaching respective conditions relative to respective thresholds or an automatic prompt generated in response to one or more monitored patient parameters exhibiting an unusual trend. In a fifth example of the method, which optionally includes one or more or each of the first through fourth examples, the patient-specific medical data comprises an indication of a pending diagnostic lab test for the patient, and wherein the portion of the communication thread that is output in response to the prompt includes a message indicating that a priority ranking of the pending diagnostic lab test has been updated in response to the one or more monitored patient parameters reaching respective conditions relative to respective thresholds or in response to the one or more monitored patient parameters exhibiting the unusual trend. In a sixth example of the method, which optionally includes one or more or each of the first through fifth examples, the prompt comprises a user input requesting display of the communication thread. In a seventh example of the method, which optionally includes one or more or each of the first through sixth examples, the patient-specific medical data comprises an indication of a status of a diagnostic lab test ordered for the patient. In an eighth example of the method, which optionally includes one or more or each of the first through seventh examples, the indication of the status of the diagnostic lab test comprises an estimated time until results are available for the diagnostic lab test, a notification that the diagnostic lab test is delayed or cancelled, or a notification that results of the diagnostic lab test are available.

Another example provides for a method for a computing device configured to execute a laboratory virtual healthcare assistant to facilitate communication between a care provider monitoring a patient and a laboratory, the method including identifying, via the laboratory virtual healthcare assistant, that a lab test has been ordered on a patient specimen of the patient, the lab test to be conducted by the laboratory; associating, via the laboratory virtual healthcare assistant, a priority ranking with the patient specimen, the priority ranking usable to place the patient specimen in a laboratory queue of other specimens to be tested; receiving one or more current patient parameters; responsive to one or more of the one or more current patient parameters reaching a predetermined condition, adjusting, via the laboratory virtual healthcare assistant, the priority ranking associated with the patient specimen; and outputting a notification of the adjusted priority ranking to the laboratory. In a first example of the method, the one or more current patient parameters are received from one or more patient monitoring devices. In a second example of the method, which optionally includes the first example, adjusting the priority ranking comprises increasing the priority ranking. In a third example of the method, which optionally includes one or both of the first and second examples, the method further includes obtaining, via the laboratory virtual healthcare assistant, an estimated time until results of the lab test on the patient specimen are available and outputting an indication of the estimated time into a communication thread viewable by the care provider. In a fourth example of the method, which optionally includes one or more or each of the first through third examples, the method further includes, before the lab test is ordered, outputting a notification into a communication thread viewable by the care provider suggesting that the care provider order the lab test, the lab test suggested based on the current patient parameters, patient medical history, patient demographic information, and/or patient lifestyle information, and further based on historical information for a plurality of prior patients. In a fifth example of the method, which optionally includes one or more or each of the first through fourth examples, the lab test is a first lab test, and further comprising identifying, via the laboratory virtual healthcare assistant, that a second lab test was ordered for the patient within a threshold amount of time from the first lab test, and if the first lab test and second lab test are identical, outputting a notification indicating that duplicate lab tests have been ordered into a communication thread viewable by the care provider. In a sixth example of the method, which optionally includes one or more or each of the first through fifth examples, the lab test is a first lab test, and the method further includes identifying, via the laboratory virtual healthcare assistant, that the first lab test is to be conducted only after a second lab test has been conducted, and if the second lab test has not been conducted on the patient, outputting a notification indicating that the first lab test is out of order into a communication thread viewable by the care provider.

An example provides for a computing device including a display screen, the computing device being configured to display on the screen a communication thread, and additionally being configured to display on the screen a dashboard that can be reached directly from the communication thread, wherein the communication thread displays communication between a care provider and a lab virtual healthcare assistant, the communication thread including diagnostic lab test information of a patient, at least a portion of the displayed diagnostic lab test information being selectable to launch the dashboard and enable the selected diagnostic lab test information to be seen within the dashboard, and wherein the communication thread is displayed while the dashboard is in an un-launched state. In a first example of the computing device, the displayed diagnostic lab test information includes a notification that results of the diagnostic lab test are available, and wherein the results are displayed within the dashboard. In a second example of the computing device, which optionally includes the first example, the communication thread includes a first message including a request from the care provider for an estimated time until results are available for a diagnostic lab test ordered for the patient and a second message including the estimated time from the lab virtual healthcare assistant. In a third example of the computing device, which optionally includes the second example, the communication thread includes a first message including a request for suggested lab tests to be conducted on the patient from the care provider and a second message including the suggested lab tests from the lab virtual healthcare assistant.

In another representation, a system includes a display and a computing device operably coupled to the display and storing instructions executable to output to the display a portion of a communication thread, where the communication thread includes communication among one or more care providers monitoring the patient and a lab virtual healthcare assistant. In a first example of the system, the portion of the communication thread includes a first message including a request for a status of a lab test ordered for the patient from a care provider of the one or more care providers to the lab virtual healthcare assistant and a second message including the status of the lab test sent from the lab virtual healthcare assistant, the lab virtual healthcare assistant configured to determine the status of the lab test from information obtained from a lab system of a laboratory conducting the lab test. In a second example of the system, which optionally includes the first example, the communication thread includes communication among the one or more care providers, lab virtual healthcare assistant, and a guideline virtual healthcare assistant, wherein the portion of the communication thread includes a first message sent by the guideline virtual healthcare assistant to the one or more care providers, the first message including guidelines for diagnosing a patient state, and wherein the lab virtual healthcare assistant is configured to track a status of one or more lab tests ordered by the one or more care providers and output a second message into the communication thread alerting the one or more care providers if the status of the one or more lab tests changes or if the one or more lab tests diverge from the guidelines.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method, comprising:
generating a patient-specific collaboration channel comprising a patient-specific dashboard and a communication thread between a care provider team monitoring a patient and a virtual healthcare assistant;
storing, at the channel, text- and/or rich media-based messages on the communication thread between one or more care providers of the care provider team and the virtual healthcare assistant regarding the patient, at least a portion of the messages on the communication thread including patient-specific medical data;

outputting, to a display device, a collaborative system interface that includes a respective patient link for each of a plurality of patients, including a first patient link for the patient; and responsive to a prompt, outputting at least a portion of the communication thread that includes the patient-specific medical data to the display device, wherein the prompt includes user selection of the first patient link from the collaborative system interface, the first patient link including a notification that a new message is available to view on the communication thread, and wherein the at least the portion of the communication thread includes diagnostic lab test information that is selectable to launch the dashboard to enable the selected diagnostic lab test information to be seen within the dashboard.

2. The method of claim 1, wherein the messages of the communication thread include a first message that comprises one or more possible diagnostic lab tests suggested by the virtual healthcare assistant to diagnose a condition of the patient, the virtual healthcare assistant utilizing a machine learning testing model to suggest the one or more possible diagnostic lab tests.

3. The method of claim 2, wherein the one or more possible diagnostic lab tests are suggested by the virtual healthcare assistant based on current monitored patient parameters, patient medical history, patient demographic information, and/or patient lifestyle information, and further based on historical information for a plurality of prior patients.

4. The method of claim 3, wherein the historical information for the plurality of prior patients comprises, for each prior patient, monitored patient parameters, patient medical history, patient demographic information, and/or patient lifestyle information, and further includes known patient outcomes for each prior patient.

5. The method of claim 2, wherein the messages of the communication thread include a second message that comprises an indication of a pending diagnostic lab test for the patient, and a third message indicating that a priority ranking of the pending diagnostic lab test has been updated in response to one or more monitored patient parameters reaching respective conditions relative to respective thresholds or in response to the one or more monitored patient parameters exhibiting an unusual trend.

6. The method of claim 5, wherein the messages of the communication thread include a fourth message that comprises an indication of a status of a diagnostic lab test ordered for the patient.

7. The method of claim 6, wherein the diagnostic lab test information in the communication thread is included in the new message that comprises a notification that results of the diagnostic lab test are available.

8. The method of claim 7, wherein the indication of the status of the diagnostic lab test comprises an estimated time until results are available for the diagnostic lab test or a notification that the diagnostic lab test is delayed or cancelled, or a notification that results of the diagnostic lab test are available.

9. A method for a computing device configured to execute a laboratory virtual healthcare assistant to facilitate communication between a care provider monitoring a patient and a laboratory, the method comprising:

before a lab test is ordered, outputting a first notification into a communication thread displayed on a display device and viewable by the care provider suggesting that the care provider order the lab test, the lab test suggested by the laboratory virtual healthcare assistant based on current patient parameters, patient medical history, patient demographic information, and/or patient lifestyle information, and further based on historical information for a plurality of prior patients;

identifying, via the laboratory virtual healthcare assistant, that the lab test has been ordered on a patient specimen of the patient, the lab test to be conducted by the laboratory;

associating, via the laboratory virtual healthcare assistant, a priority ranking with the patient specimen, the priority ranking usable to place the patient specimen in a laboratory queue of other specimens to be tested;

receiving one or more further current patient parameters;

responsive to one or more of the one or more further current patient parameters reaching a predetermined condition, adjusting, via the laboratory virtual healthcare assistant, the priority ranking associated with the patient specimen;

outputting a second notification of the adjusted priority ranking to the laboratory and outputting, via the laboratory virtual healthcare assistant, a third notification of the adjusted priority ranking into the communication thread;

outputting, via the laboratory virtual healthcare assistant, a fourth notification into the communication thread that results of the lab test are available; and receiving a user input selecting the fourth notification, and in response, displaying on the display device a dashboard viewable by the care provider, the dashboard displaying the results of the lab test along with additional information specific to the patient.

10. The method of claim 9, wherein the one or more further current patient parameters are received from one or more patient monitoring devices.

11. The method of claim 9, wherein adjusting the priority ranking comprises increasing the priority ranking.

12. The method of claim 9, further comprising obtaining, via the laboratory virtual healthcare assistant, an estimated time until results of the lab test on the patient specimen are available and outputting an indication of the estimated time into the communication thread viewable by the care provider.

13. The method of claim 9, wherein the communication thread includes an identifier of the patient displayed on the display device and multiple messages displayed on the display device between at least the care provider and the laboratory virtual healthcare assistant regarding the patient, the multiple messages including the first notification, the third notification, and the fourth notification.

14. The method of claim 9, wherein the lab test is a first lab test, and further comprising identifying, via the laboratory virtual healthcare assistant, that a second lab test was ordered for the patient within a threshold amount of time from the first lab test, and if the first lab test and second lab test are identical, outputting a notification indicating that duplicate lab tests have been ordered into the communication thread viewable by the care provider.

15. The method of claim 9, wherein the dashboard is displayed in response to a first type of user input applied to select the fourth notification, and further comprising displaying, in response to a second type of user input applied to select the fourth notification, a preview of the results of the lab test without displaying the dashboard.

* * * * *